(12) United States Patent
Ishimaru et al.

(10) Patent No.: US 8,945,864 B2
(45) Date of Patent: Feb. 3, 2015

(54) METHOD OF DETERMINING 1,5-ANHYDROGLUCITOL, AND REAGENT COMPOSITION FOR DETERMINING 1,5-ANHYDROGLUCITOL

(75) Inventors: Emi Ishimaru, Fukuyama (JP); Hirokazu Sanada, Mihara (JP); Hironori Omura, Fukuyama (JP); Hideki Yoshioka, Takasaki (JP); Shuhei Tsukamoto, Takasaki (JP); Minoru Masuda, Ageo (JP)

(73) Assignees: Ikeda Food Research Co., Ltd., Fukuyama-Shi (JP); Nippon Kayaku Kabushiki Kaisha, Tokyo (JP)

( * ) Notice: Subject to any disclaimer, the term of this patent is extended or adjusted under 35 U.S.C. 154(b) by 1032 days.

(21) Appl. No.: 12/305,941

(22) PCT Filed: Jun. 22, 2007

(86) PCT No.: PCT/JP2007/062623
§ 371 (c)(1),
(2), (4) Date: Dec. 19, 2008

(87) PCT Pub. No.: WO2007/148797
PCT Pub. Date: Dec. 27, 2007

(65) Prior Publication Data
US 2010/0173343 A1    Jul. 8, 2010

(30) Foreign Application Priority Data

Jun. 22, 2006  (JP) ................. 2006-172619

(51) Int. Cl.
| | | |
|---|---|---|
| *C12Q 1/32* | (2006.01) | |
| *C12N 9/04* | (2006.01) | |
| *C12P 21/06* | (2006.01) | |
| *C12P 21/04* | (2006.01) | |
| *C12N 15/00* | (2006.01) | |
| *C07H 21/04* | (2006.01) | |
| *C12Q 1/66* | (2006.01) | |
| *G01N 33/68* | (2006.01) | |

(52) U.S. Cl.
CPC .............. *C12Q 1/32* (2013.01); *C12N 9/0006* (2013.01); *C12Q 1/66* (2013.01); *G01N 33/6893* (2013.01); *G01N 2800/042* (2013.01)
USPC ............ 435/26; 435/190; 435/440; 435/69.1; 435/71.1; 536/23.2

(58) Field of Classification Search
CPC .................. C12Q 1/32; C12N 9/0006
See application file for complete search history.

(56) References Cited

U.S. PATENT DOCUMENTS

| | | | |
|---|---|---|---|
| 4,810,640 A | 3/1989 | Nakamura et al. | |
| 4,916,069 A | 4/1990 | Fujiwara et al. | |
| 4,994,377 A | 2/1991 | Nakamura et al. | |
| RE34,851 E | 2/1995 | Manning et al. | |
| 5,407,806 A | 4/1995 | Yabuuchi et al. | |
| 5,426,033 A | 6/1995 | Kojima et al. | |
| 5,468,380 A | 11/1995 | Yabuuchi et al. | |
| 5,468,621 A | 11/1995 | Kojima et al. | |
| 5,486,458 A | 1/1996 | Kojima et al. | |
| 5,541,108 A | 7/1996 | Fujiwara et al. | |
| 5,753,481 A | 5/1998 | Niwa et al. | |
| 5,834,263 A | 11/1998 | Niwa et al. | |
| 5,861,292 A | 1/1999 | Niwa et al. | |
| 5,871,949 A | 2/1999 | Ebinuma et al. | |
| 5,888,786 A | 3/1999 | Niwa et al. | |
| 6,153,419 A | 11/2000 | Aisaka et al. | |
| 6,268,166 B1 | 7/2001 | Kojima et al. | |
| 6,309,852 B1 | 10/2001 | Tazoe et al. | |
| 6,448,029 B1 | 9/2002 | Tazoe et al. | |

FOREIGN PATENT DOCUMENTS

| | | |
|---|---|---|
| DE | 102004010131 A1 | 9/2005 |
| JP | 02042980 | 2/1990 |
| JP | 05236995 | 9/1993 |
| JP | 05344900 | 12/1993 |
| JP | 06303995 | 11/1994 |
| JP | 07067697 | 3/1995 |
| JP | 11018762 | 1/1999 |
| JP | 2000-135079 A | 5/2000 |
| JP | 2001078797 | 3/2001 |
| JP | 2007300818 | 11/2007 |
| WO | WO-94/20609 A | 9/1994 |
| WO | WO-95/23220 A | 8/1995 |
| WO | 03008588 | 1/2003 |

OTHER PUBLICATIONS

Branden et al. Introduction to Protein Structure, Garland Publishing Inc., New York, p. 247, 1991.*
UniProt: Q92YU0_RHIME Q92YU0 Dehydrogenase, FAD-dependent OS=*Rhizobium meliloti*, Dec. 1, 2001, sequence version1.
Chinese Office Action mailed Oct. 27, 2010 for the corresponding Chinese patent application No. No. 200780023052.9.
Risnsho-Kensa vol. 33, No. 8, pp. 901-907. (1989).
Yoshitaka Morishita et al., "III—Test method for diagnosis of diabetes mellitus", Medical Technology (extra-edition) 2002, vol. 30, No. 13, pp. 1498-1499.

(Continued)

*Primary Examiner* — Yong Pak
(74) *Attorney, Agent, or Firm* — Leason Ellis LLP.

(57) ABSTRACT

The object of the present invention is to provide a method of determining 1,5-anhydroglucitol, including using (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% with the amino acid sequence of SEQ ID NO: 2 and which has sorbose dehydrogenase activity.

10 Claims, 8 Drawing Sheets

(56) References Cited

OTHER PUBLICATIONS

Yoshimasa Saito et al., "Cloning of Genes Coding for L-Sorbose and L-Sorbosone Dehydrogenases from *Gluconobacter oxydans* and Microbial Production of 2-Keto-L-Gulonate, a Precursor of L-Ascorbic Acid, in a Recombinant *G. oxydans* Strain", Applied and Environ. Microbiology, Feb. 1997, p. 454-460.

I. Kitamura et al., "Conversion of L-Sorbose to L-Sorbosone by *Gluconobacter melanogenus*", Biotechnology and Bioengineering, No. 17, p. 349-359 (1975).

Kiyoshi Sato et al., "Enzymatic Studies on the Oxidation of Sugar and Sugar Alcohol", The Journal of Biochemistry, 1969, vol. 66, No. 4, p. 521-527.

National Center for Biotechnology Information (NCBI), Accession No. NC 436019, Dec. 3, 2005, uploaded, retrieval date Aug. 13, 2007.

"Particle-bound L-Sorbose Dehydrogenase from *Acetobacter syboxydans*", Agr. Biol. Chem., vol. 31, No. 5, p. 640-641, 1967.

M. Yabuuchi et al., Simple Enzymatic Method for Determining 1,5-Anhydro-D-glucitol in Plasma for Diagnosis of Diabetes Mellitus, Clinical Chemistry, 1989, vol. 35, No. 10, pp. 2039-2043.

Notice of Allowance mailed Feb. 19, 2013 for the related Japanese Application No. 2008-522549.

National Center for Biotechnology Information (NCBI), Accession No. NP_436019, Dec. 3, 2005, uploaded, retrieval date Aug. 13, 2007.

* cited by examiner

SEQUENCE LISTING

```
<160> NUMBER OF SEQ ID NOS: 10

<210> SEQ ID NO 1
<211> LENGTH: 1596
<212> TYPE: DNA
<213> ORGANISM: Sinorhizobium sp. 97507
<220> FEATURE:
<221> NAME/KEY: CDS
<222> LOCATION: (1)..(1596)

<400> SEQUENCE: 1 atg atg gaa ggt ttt gat tac gtc atc gtc ggc ggc gga tcg tcg ggc      48
Met Met Glu Gly Phe Asp Tyr Val Ile Val Gly Gly Gly Ser Ser Gly
 1               5                  10                  15 tgc gtt ctg gcc gcc cgc ctt tcc gag aac cct tcg gtg cgc gtc tgc      96
Cys Val Leu Ala Ala Arg Leu Ser Glu Asn Pro Ser Val Arg Val Cys
            20                  25                  30 ctg atc gag gcg ggc ggg cgc gac cgt cac ccg ttg atc cac atg ccg     144
Leu Ile Glu Ala Gly Gly Arg Asp Arg His Pro Leu Ile His Met Pro
        35                  40                  45 gtc ggc ttc gca aag ctg acc gcg ggg ccg atg acc tgg ggc ctg acg     192
Val Gly Phe Ala Lys Leu Thr Ala Gly Pro Met Thr Trp Gly Leu Thr
    50                  55                  60
```

```
acc gcc ccg cag aaa cat gca aac aac cgc gag att ccc tat gcc cag      240
Thr Ala Pro Gln Lys His Ala Asn Asn Arg Glu Ile Pro Tyr Ala Gln
 65              70                  75                  80 gcg aga gtg ctc ggc gga ggg tcc tcg atc aat gcc gag gtc tat acg      288
Ala Arg Val Leu Gly Gly Gly Ser Ser Ile Asn Ala Glu Val Tyr Thr
                 85                  90                  95 cgc ggc cac ccg cgg gac tat gac cgc tgg gtg gaa gag ggg gcc gac      336
Arg Gly His Pro Arg Asp Tyr Asp Arg Trp Val Glu Glu Gly Ala Asp
            100                 105                 110 gga tgg agc ttt cag gag gtg aag cct tac ttc ctg cga tcc gag ggc      384
Gly Trp Ser Phe Gln Glu Val Lys Pro Tyr Phe Leu Arg Ser Glu Gly
        115                 120                 125 aat acg atc ctc tcc ggc gag tgg cac ggg acg gac ggt cct ctc gga      432
Asn Thr Ile Leu Ser Gly Glu Trp His Gly Thr Asp Gly Pro Leu Gly
    130                 135                 140 gtc tcc aac ctt ccc gat ccg cag ccg atg aca cgg gct ttc gtc cag      480
Val Ser Asn Leu Pro Asp Pro Gln Pro Met Thr Arg Ala Phe Val Gln
145                 150                 155                 160 agc tgc cag gaa ctc ggc atc ccc tat aat ccc gac ttc aac ggg ccg      528
Ser Cys Gln Glu Leu Gly Ile Pro Tyr Asn Pro Asp Phe Asn Gly Pro
                165                 170                 175 gtc cag gaa ggt gcg ggg gtc tac cag acg acg atc cgc aac agc cgc      576
Val Gln Glu Gly Ala Gly Val Tyr Gln Thr Thr Ile Arg Asn Ser Arg
            180                 185                 190 cgt tgc tcg gcc gct gtc gga tat ttg cgg ccg gcg ctc gcg cgc aag      624
Arg Cys Ser Ala Ala Val Gly Tyr Leu Arg Pro Ala Leu Ala Arg Lys
        195                 200                 205 aac ctc atg ctc atc acg ggt gcg ctt gtg ctg cgc atc gta ttc cag      672
Asn Leu Met Leu Ile Thr Gly Ala Leu Val Leu Arg Ile Val Phe Gln
    210                 215                 220 ggc cgc cgc gcc gtc ggc gtc gaa tac tcg acc ggg ggc gcc gcg aag      720
Gly Arg Arg Ala Val Gly Val Glu Tyr Ser Thr Gly Gly Ala Ala Lys
225                 230                 235                 240 atc gcc cgg gcg gaa agc gag gtt ctc gtc acc tcg ggt gcg atc gga      768
Ile Ala Arg Ala Glu Ser Glu Val Leu Val Thr Ser Gly Ala Ile Gly
                245                 250                 255 acg cct aag ctc atg atg ctt tca ggc gtc ggc ccg gcc gcc tct ctg      816
Thr Pro Lys Leu Met Met Leu Ser Gly Val Gly Pro Ala Ala Ser Leu
            260                 265                 270 cgg agc cac ggt atc gac gtc gtg cag gat atg gcg ggg gtc ggc cag      864
Arg Ser His Gly Ile Asp Val Val Gln Asp Met Ala Gly Val Gly Gln
        275                 280                 285 aac ctc cac gat cac ttc ggc gtg gac atc gtt gcc gaa ctg aag ggg      912
Asn Leu His Asp His Phe Gly Val Asp Ile Val Ala Glu Leu Lys Gly
    290                 295                 300 cat gac agc ctc gac aag tac aac aag ttc cac tgg atg ctc ttg gcg      960
His Asp Ser Leu Asp Lys Tyr Asn Lys Phe His Trp Met Leu Leu Ala
305                 310                 315                 320 gga atc gaa tac gcg ctt ttc aaa tcc ggg ccg gtc gcc tcg aat gtt     1008
Gly Ile Glu Tyr Ala Leu Phe Lys Ser Gly Pro Val Ala Ser Asn Val
                325                 330                 335 gtg gag ggt gga gcc ttc tgg tac ggc gat agg gca agc ccc tat ccc     1056
Val Glu Gly Gly Ala Phe Trp Tyr Gly Asp Arg Ala Ser Pro Tyr Pro
            340                 345                 350 gac ctg caa ttc cac ttt ctt gcg ggg gcg gga gcc gag gcc ggg gtg     1104
Asp Leu Gln Phe His Phe Leu Ala Gly Ala Gly Ala Glu Ala Gly Val
        355                 360                 365 ccg agc gtc cca aag ggt tcc tcc ggc gtg acc ttg aat tcc tac acg     1152
Pro Ser Val Pro Lys Gly Ser Ser Gly Val Thr Leu Asn Ser Tyr Thr
```

```
                   370               375               380
gtc cgg ccg aag tca cgg ggt tcc gtc acc ctt cgt tct gcc gac ccc    1200
Val Arg Pro Lys Ser Arg Gly Ser Val Thr Leu Arg Ser Ala Asp Pro
385               390               395               400 cgt gcc ctg ccg atc gtc gac ccg aac ttc ctc gat gat ccg gat gat    1248
Arg Ala Leu Pro Ile Val Asp Pro Asn Phe Leu Asp Asp Pro Asp Asp
            405               410               415 ctc agg atc tcg gtc gaa ggc atc agg atc agc agg gaa att ttc ggg    1296
Leu Arg Ile Ser Val Glu Gly Ile Arg Ile Ser Arg Glu Ile Phe Gly
        420               425               430 cag ccg tcg ctg cag aag tac atc aag acg atc cgc ttc ccc gac gag    1344
Gln Pro Ser Leu Gln Lys Tyr Ile Lys Thr Ile Arg Phe Pro Asp Glu
    435               440               445 agc gtc agg aca cag gcc gac ttc gag gcc tat gcg cgg caa tac ggg    1392
Ser Val Arg Thr Gln Ala Asp Phe Glu Ala Tyr Ala Arg Gln Tyr Gly
450               455               460 cgg acg tcc tat cac ccg aca tgc acc tgc aag atg ggt cgc gac gat    1440
Arg Thr Ser Tyr His Pro Thr Cys Thr Cys Lys Met Gly Arg Asp Asp
465               470               475               480 atg tcg gtg gtc gat ccg cag ctc cgc gtc cac ggc ctt gac ggc atc    1488
Met Ser Val Val Asp Pro Gln Leu Arg Val His Gly Leu Asp Gly Ile
            485               490               495 cgc atc tgc gac agt tcg gtg atg ccc agt ctc gtg ggc tcc aat acc    1536
Arg Ile Cys Asp Ser Ser Val Met Pro Ser Leu Val Gly Ser Asn Thr
        500               505               510 aat gcg gct acc atc atg atc ggc gag aag gcg gcc gat ctg ata cgg    1584
Asn Ala Ala Thr Ile Met Ile Gly Glu Lys Ala Ala Asp Leu Ile Arg
    515               520               525 ggc aac att tga                                                    1596
Gly Asn Ile
530

<210> SEQ ID NO 2
<211> LENGTH: 531
<212> TYPE: PRT
<213> ORGANISM: Sinorhizobium sp. 97507

<400> SEQUENCE: 2

Met Met Glu Gly Phe Asp Tyr Val Ile Val Gly Gly Ser Ser Gly
1               5                  10                  15

Cys Val Leu Ala Ala Arg Leu Ser Glu Asn Pro Ser Val Arg Val Cys
            20                  25                  30

Leu Ile Glu Ala Gly Gly Arg Asp Arg His Pro Leu Ile His Met Pro
        35                  40                  45

Val Gly Phe Ala Lys Leu Thr Ala Gly Pro Met Thr Trp Gly Leu Thr
    50                  55                  60

Thr Ala Pro Gln Lys His Ala Asn Asn Arg Glu Ile Pro Tyr Ala Gln
65                  70                  75                  80

Ala Arg Val Leu Gly Gly Ser Ser Ile Asn Ala Glu Val Tyr Thr
            85                  90                  95

Arg Gly His Pro Arg Asp Tyr Asp Arg Trp Val Glu Glu Gly Ala Asp
        100                 105                 110

Gly Trp Ser Phe Gln Glu Val Lys Pro Tyr Phe Leu Arg Ser Glu Gly
    115                 120                 125

Asn Thr Ile Leu Ser Gly Glu Trp His Gly Thr Asp Gly Pro Leu Gly
130                 135                 140

Val Ser Asn Leu Pro Asp Pro Gln Pro Met Thr Arg Ala Phe Val Gln
145                 150                 155                 160
```

```
Ser Cys Gln Glu Leu Gly Ile Pro Tyr Asn Pro Asp Phe Asn Gly Pro
                165                 170                 175

Val Gln Glu Gly Ala Gly Val Tyr Gln Thr Thr Ile Arg Asn Ser Arg
            180                 185                 190

Arg Cys Ser Ala Ala Val Gly Tyr Leu Arg Pro Ala Leu Ala Arg Lys
        195                 200                 205

Asn Leu Met Leu Ile Thr Gly Ala Leu Val Leu Arg Ile Val Phe Gln
    210                 215                 220

Gly Arg Arg Ala Val Gly Val Glu Tyr Ser Thr Gly Ala Ala Lys
225                 230                 235                 240

Ile Ala Arg Ala Glu Ser Glu Val Leu Val Thr Ser Gly Ala Ile Gly
                245                 250                 255

Thr Pro Lys Leu Met Met Leu Ser Gly Val Gly Pro Ala Ala Ser Leu
            260                 265                 270

Arg Ser His Gly Ile Asp Val Gln Asp Met Ala Gly Val Gly Gln
        275                 280                 285

Asn Leu His Asp His Phe Gly Val Asp Ile Val Ala Glu Leu Lys Gly
    290                 295                 300

His Asp Ser Leu Asp Lys Tyr Asn Lys Phe His Trp Met Leu Leu Ala
305                 310                 315                 320

Gly Ile Glu Tyr Ala Leu Phe Lys Ser Gly Pro Val Ala Ser Asn Val
                325                 330                 335

Val Glu Gly Gly Ala Phe Trp Tyr Gly Asp Arg Ala Ser Pro Tyr Pro
            340                 345                 350

Asp Leu Gln Phe His Phe Leu Ala Gly Ala Gly Ala Glu Ala Gly Val
        355                 360                 365

Pro Ser Val Pro Lys Gly Ser Ser Gly Val Thr Leu Asn Ser Tyr Thr
    370                 375                 380

Val Arg Pro Lys Ser Arg Gly Ser Val Thr Leu Arg Ser Ala Asp Pro
385                 390                 395                 400

Arg Ala Leu Pro Ile Val Asp Pro Asn Phe Leu Asp Pro Asp Asp
                405                 410                 415

Leu Arg Ile Ser Val Glu Gly Ile Arg Ile Ser Arg Glu Ile Phe Gly
        420                 425                 430

Gln Pro Ser Leu Gln Lys Tyr Ile Lys Thr Ile Arg Phe Pro Asp Glu
    435                 440                 445

Ser Val Arg Thr Gln Ala Asp Phe Glu Ala Tyr Ala Arg Gln Tyr Gly
    450                 455                 460

Arg Thr Ser Tyr His Pro Thr Cys Thr Cys Lys Met Gly Arg Asp Asp
465                 470                 475                 480

Met Ser Val Val Asp Pro Gln Leu Arg Val His Gly Leu Asp Gly Ile
                485                 490                 495

Arg Ile Cys Asp Ser Ser Val Met Pro Ser Leu Val Gly Ser Asn Thr
        500                 505                 510

Asn Ala Ala Thr Ile Met Ile Gly Glu Lys Ala Ala Asp Leu Ile Arg
    515                 520                 525

Gly Asn Ile
    530

<210> SEQ ID NO 3
<211> LENGTH: 30
<212> TYPE: DNA
<213> ORGANISM: Artificial Sequence
<220> FEATURE:
```

<223> OTHER INFORMATION: primer

<400> SEQUENCE: 3 cccccccatgg atgatggaag gttttgatta    30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gggaagcttt caaatgttgc cccgtatcag    30

<210> SEQ ID NO 5
<211> LENGTH: 1602
<212> TYPE: DNA
<213> ORGANISM: Sinorhizobium sp. 97507
<220> FEATURE:
<221> NAME/KEY: CDS
<222> LOCATION: (1)..(1602)

<400> SEQUENCE: 5

| | | |
|---|---|---|
| atg gaa ttc atg gaa ggt ttt gat tac gtc atc gtc ggc ggc gga tcg<br>Met Glu Phe Met Glu Gly Phe Asp Tyr Val Ile Val Gly Gly Gly Ser<br>1               5                   10                  15 | 48 |
| tcg ggc tgt gtt ctg gcc gcc cgc ctt tcc gag aac cct tcg gtg cgc<br>Ser Gly Cys Val Leu Ala Ala Arg Leu Ser Glu Asn Pro Ser Val Arg<br>            20                  25                  30 | 96 |
| gtc tgc ctg atc gag gca ggg cgc gac cgt cac ccg ttg atc cac<br>Val Cys Leu Ile Glu Ala Gly Arg Asp Arg His Pro Leu Ile His<br>        35                  40                  45 | 144 |
| atg ccg gtc ggc ttc gca aag ctg acc gca ggg ccg atg acc tgg ggc<br>Met Pro Val Gly Phe Ala Lys Leu Thr Ala Gly Pro Met Thr Trp Gly<br>    50                  55                  60 | 192 |
| ctg acg acc gcc ccg cag aaa cat gca aac aac cgc gag att ccc tat<br>Leu Thr Thr Ala Pro Gln Lys His Ala Asn Asn Arg Glu Ile Pro Tyr<br>65                  70                  75                  80 | 240 |
| gcc cag gcg aga gtg ctc ggc gga ggg tcc tcg atc aat gcc gag gtc<br>Ala Gln Ala Arg Val Leu Gly Gly Gly Ser Ser Ile Asn Ala Glu Val<br>                85                  90                  95 | 288 |
| tat acg cgc ggc cac ccg cgg gac tat gac cgc tgg gtg gaa gag ggg<br>Tyr Thr Arg Gly His Pro Arg Asp Tyr Asp Arg Trp Val Glu Glu Gly<br>            100                 105                 110 | 336 |
| gcc gac gga tgg agc ttt cag gag gtg aag cct tac ttc ctg cga tcc<br>Ala Asp Gly Trp Ser Phe Gln Glu Val Lys Pro Tyr Phe Leu Arg Ser<br>        115                 120                 125 | 384 |
| gag ggc aat acg atc ctc tcc ggc gag tgg cac ggg acg gac ggt cct<br>Glu Gly Asn Thr Ile Leu Ser Gly Glu Trp His Gly Thr Asp Gly Pro<br>    130                 135                 140 | 432 |
| ctc gga gtc tcc aac ctt ccc gat ccg cag ccg atg aca cgg gct ttc<br>Leu Gly Val Ser Asn Leu Pro Asp Pro Gln Pro Met Thr Arg Ala Phe<br>145                 150                 155                 160 | 480 |
| gtc cag agc tgc cag gaa ctc ggc atc ccc tat aat ccc gac ttc aac<br>Val Gln Ser Cys Gln Glu Leu Gly Ile Pro Tyr Asn Pro Asp Phe Asn<br>                165                 170                 175 | 528 |
| ggg ccg gtc cag gaa ggt gcg ggg gtc tac cag acg acg atc cgc aac<br>Gly Pro Val Gln Glu Gly Ala Gly Val Tyr Gln Thr Thr Ile Arg Asn<br>            180                 185                 190 | 576 |
| agc cgc cgt tgc tcg gcc gct gtc gga tat ttg cgg ccg gcg ctc gcg<br>Ser Arg Arg Cys Ser Ala Ala Val Gly Tyr Leu Arg Pro Ala Leu Ala<br> | 624 |

-continued

```
                195                 200                 205
cgc aag aac ctc atg ctc atc acg ggt gcg ctt gtg ctg cgc atc gta      672
Arg Lys Asn Leu Met Leu Ile Thr Gly Ala Leu Val Leu Arg Ile Val
    210                 215                 220 ttc cag ggc cgc cgc gcc gtc ggc gtc gaa tac tcg acc ggg ggc gcc      720
Phe Gln Gly Arg Arg Ala Val Gly Val Glu Tyr Ser Thr Gly Gly Ala
225                 230                 235                 240 gcg aag atc gcc cgg gcg gaa agc gag gtt ctc gtc acc tcg ggt gcg      768
Ala Lys Ile Ala Arg Ala Glu Ser Glu Val Leu Val Thr Ser Gly Ala
                245                 250                 255 atc gga acg cct aag ctc atg atg ctt tca ggc gtc ggc ccg gcc gcc      816
Ile Gly Thr Pro Lys Leu Met Met Leu Ser Gly Val Gly Pro Ala Ala
            260                 265                 270 tct ctg cgg agc cac ggt atc gac gtc gtg cag gat atg gcg ggg gtc      864
Ser Leu Arg Ser His Gly Ile Asp Val Val Gln Asp Met Ala Gly Val
        275                 280                 285 ggc cag aac ctc cac gat cac ttc ggc gtg gac atc gtt gcc gaa ctg      912
Gly Gln Asn Leu His Asp His Phe Gly Val Asp Ile Val Ala Glu Leu
    290                 295                 300 aag ggg cat gac agc ctc gac aag tac aac aag ttc cac tgg atg ctc      960
Lys Gly His Asp Ser Leu Asp Lys Tyr Asn Lys Phe His Trp Met Leu
305                 310                 315                 320 ttg gcg gga atc gaa tac gcg ctt ttc aaa tcc ggg ccg gtc gcc tcg     1008
Leu Ala Gly Ile Glu Tyr Ala Leu Phe Lys Ser Gly Pro Val Ala Ser
                325                 330                 335 aat gtt gtg gag ggt gga gcc ttc tgg tac ggc gat agg gca agc ccc     1056
Asn Val Val Glu Gly Gly Ala Phe Trp Tyr Gly Asp Arg Ala Ser Pro
            340                 345                 350 tat ccc gac ctg caa ttc cac ttt ctt gcg ggg gcg gga gcc gag gcc     1104
Tyr Pro Asp Leu Gln Phe His Phe Leu Ala Gly Ala Gly Ala Glu Ala
        355                 360                 365 ggg gtg ccg agc gtc cca aag ggt tcc tcc ggc gtg acc ttg aat tcc     1152
Gly Val Pro Ser Val Pro Lys Gly Ser Ser Gly Val Thr Leu Asn Ser
    370                 375                 380 tac acg gtc cgg ccg aag tca cgg ggt tcc gtc acc ctt cgt tct gcc     1200
Tyr Thr Val Arg Pro Lys Ser Arg Gly Ser Val Thr Leu Arg Ser Ala
385                 390                 395                 400 gac ccc cgt gcc ctg ccg atc gtc gac ccg aac ttc ctc gat gat ccg     1248
Asp Pro Arg Ala Leu Pro Ile Val Asp Pro Asn Phe Leu Asp Asp Pro
                405                 410                 415 gat gat ctc agg atc tcg gtc gaa ggc atc agg atc agc agg gaa att     1296
Asp Asp Leu Arg Ile Ser Val Glu Gly Ile Arg Ile Ser Arg Glu Ile
            420                 425                 430 ttc ggg cag ccg tcg ctg cag aag tac atc aag acg atc cgc ttc ccc     1344
Phe Gly Gln Pro Ser Leu Gln Lys Tyr Ile Lys Thr Ile Arg Phe Pro
        435                 440                 445 gac gag agc gtc agg aca cag gcc gac ttc gag gcc tat gcg cgg caa     1392
Asp Glu Ser Val Arg Thr Gln Ala Asp Phe Glu Ala Tyr Ala Arg Gln
    450                 455                 460 tac ggg cgg acg tcc tat cac ccg aca tgc acc tgc aag atg ggt cgc     1440
Tyr Gly Arg Thr Ser Tyr His Pro Thr Cys Thr Cys Lys Met Gly Arg
465                 470                 475                 480 gac gat atg tcg gtg gtc gat ccg cag ctc cgc gtc cac ggc ctt gac     1488
Asp Asp Met Ser Val Val Asp Pro Gln Leu Arg Val His Gly Leu Asp
                485                 490                 495 ggc atc cgc atc tgc gac agt tcg gtg atg ccc agt ctc gtg ggc tcc     1536
Gly Ile Arg Ile Cys Asp Ser Ser Val Met Pro Ser Leu Val Gly Ser
            500                 505                 510 aat acc aat gcg gct acc atc atg atc ggc gag aag gcg gcc gat ctg     1584
```

```
Asn Thr Asn Ala Ala Thr Ile Met Ile Gly Glu Lys Ala Asp Leu
            515                 520                 525 ata cgg ggc aac att tga                                          1602
Ile Arg Gly Asn Ile
    530
```

<210> SEQ ID NO 6
<211> LENGTH: 533
<212> TYPE: PRT
<213> ORGANISM: Sinorhizobium sp. 97507

<400> SEQUENCE: 6

```
Met Glu Phe Met Glu Gly Phe Asp Tyr Val Ile Val Gly Gly Ser
  1               5                  10                  15

Ser Gly Cys Val Leu Ala Ala Arg Leu Ser Glu Asn Pro Ser Val Arg
             20                  25                  30

Val Cys Leu Ile Glu Ala Gly Gly Arg Asp Arg His Pro Leu Ile His
         35                  40                  45

Met Pro Val Gly Phe Ala Lys Leu Thr Ala Gly Pro Met Thr Trp Gly
     50                  55                  60

Leu Thr Thr Ala Pro Gln Lys His Ala Asn Asn Arg Glu Ile Pro Tyr
 65                  70                  75                  80

Ala Gln Ala Arg Val Leu Gly Gly Ser Ser Ile Asn Ala Glu Val
                 85                  90                  95

Tyr Thr Arg Gly His Pro Arg Asp Tyr Asp Arg Trp Val Glu Gly
                100                 105                 110

Ala Asp Gly Trp Ser Phe Gln Glu Val Lys Pro Tyr Phe Leu Arg Ser
            115                 120                 125

Glu Gly Asn Thr Ile Leu Ser Gly Glu Trp His Gly Thr Asp Gly Pro
        130                 135                 140

Leu Gly Val Ser Asn Leu Pro Asp Pro Gln Pro Met Thr Arg Ala Phe
145                 150                 155                 160

Val Gln Ser Cys Gln Glu Leu Gly Ile Pro Tyr Asn Pro Asp Phe Asn
                165                 170                 175

Gly Pro Val Gln Glu Gly Ala Gly Val Tyr Gln Thr Thr Ile Arg Asn
            180                 185                 190

Ser Arg Arg Cys Ser Ala Ala Val Gly Tyr Leu Arg Pro Ala Leu Ala
        195                 200                 205

Arg Lys Asn Leu Met Leu Ile Thr Gly Ala Leu Val Leu Arg Ile Val
    210                 215                 220

Phe Gln Gly Arg Arg Ala Val Gly Val Glu Tyr Ser Thr Gly Gly Ala
225                 230                 235                 240

Ala Lys Ile Ala Arg Ala Glu Ser Glu Val Leu Val Thr Ser Gly Ala
                245                 250                 255

Ile Gly Thr Pro Lys Leu Met Met Leu Ser Gly Val Gly Pro Ala Ala
            260                 265                 270

Ser Leu Arg Ser His Gly Ile Asp Val Val Gln Asp Met Ala Gly Val
        275                 280                 285

Gly Gln Asn Leu His Asp His Phe Gly Val Asp Ile Val Ala Glu Leu
    290                 295                 300

Lys Gly His Asp Ser Leu Asp Lys Tyr Asn Lys Phe His Trp Met Leu
305                 310                 315                 320

Leu Ala Gly Ile Glu Tyr Ala Leu Phe Lys Ser Gly Pro Val Ala Ser
                325                 330                 335

Asn Val Val Glu Gly Gly Ala Phe Trp Tyr Gly Asp Arg Ala Ser Pro
```

```
            340                 345                 350
Tyr Pro Asp Leu Gln Phe His Phe Leu Ala Gly Ala Gly Ala Glu Ala
        355                 360                 365

Gly Val Pro Ser Val Pro Lys Gly Ser Ser Gly Val Thr Leu Asn Ser
    370                 375                 380

Tyr Thr Val Arg Pro Lys Ser Arg Gly Ser Val Thr Leu Arg Ser Ala
385                 390                 395                 400

Asp Pro Arg Ala Leu Pro Ile Val Asp Pro Asn Phe Leu Asp Asp Pro
                405                 410                 415

Asp Asp Leu Arg Ile Ser Val Glu Gly Ile Arg Ile Ser Arg Glu Ile
            420                 425                 430

Phe Gly Gln Pro Ser Leu Gln Lys Tyr Ile Lys Thr Ile Arg Phe Pro
        435                 440                 445

Asp Glu Ser Val Arg Thr Gln Ala Asp Phe Glu Ala Tyr Ala Arg Gln
    450                 455                 460

Tyr Gly Arg Thr Ser Tyr His Pro Thr Cys Thr Cys Lys Met Gly Arg
465                 470                 475                 480

Asp Asp Met Ser Val Val Asp Pro Gln Leu Arg Val His Gly Leu Asp
                485                 490                 495

Gly Ile Arg Ile Cys Asp Ser Ser Val Met Pro Ser Leu Val Gly Ser
            500                 505                 510

Asn Thr Asn Ala Ala Thr Ile Met Ile Gly Glu Lys Ala Ala Asp Leu
        515                 520                 525

Ile Arg Gly Asn Ile
    530
```

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
atataccatg gaattcatgg aaggttttga ttacg                       35

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
atctagagga tcctcatcaa atgttgcccc gtatc                       35

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
atatagatct tgacagctta tcatcgactg c                           31

<210> SEQ ID NO 10
<211> LENGTH: 30
<212> TYPE: DNA
<213> ORGANISM: Artificial Sequence

```
<220> FEATURE:
<223> OTHER INFORMATION: primer

<400> SEQUENCE: 10
attaagatct cagataaaac gaaaggccca                                          30
```

METHOD OF DETERMINING 1,5-ANHYDROGLUCITOL, AND REAGENT COMPOSITION FOR DETERMINING 1,5-ANHYDROGLUCITOL

CROSS REFERENCE TO RELATED APPLICATION

This is a U.S. national phase application under 35 U.S.C. §371 of International Patent Application No. PCT/JP2007/062623 filed Jun. 22, 2007 and claims the benefit of Japanese Application No. JP2006-172619, filed Jun. 22, 2006. The International Application was published on Dec. 27, 2007 as International Publication No. WO/2007/148797 A1 under PCT Article 21(2) the content of both applications are incorporated herein in their entirety.

TECHNICAL FIELD

The present invention relates to a method of determining 1,5-anhydroglucitol and a reagent composition for determining 1,5-anhydroglucitol.

BACKGROUND ART 1,5-Anhydroglucitol (hereinafter, referred to as "1,5-AG") is a reduced form of glucose where the C1 position is reduced, and a small amount of 1,5-AG is present in the living body. It was discovered that 1,5-AG is a useful control marker for diabetes (for example, see Non-patent Document 1 or 2).

As described in Non-patent Document 1,1,5-AG may be a marker ranked somewhere between the blood glucose level and hemoglobin A1c (HbA1c). Therefore, it is considered that the 1,5-AG level in blood could be a suitable marker for mild diabetic patients in their self-management of the disease.

TABLE 1

| Marker | Characteristics |
| --- | --- |
| Blood glucose level | May erratically fluctuate up and down for a short time. |
| 1,5-AG | Indicates the blood glucose level from about five to seven days before the test. |
| HbA1c | Indicates the mean glucose level from about two months before the test. |

As disclosed in Non-patent Document 2, the 1,5-AG level in normal healthy people indicates a monosaccharide component that is the second most abundant in the blood after glucose. According to a clinical investigation conducted on a Japanese population, the average level of 1,5-AG is 24.6±7.2 (mean±SD) µg/ml. The physiologically-fluctuating range among individuals is small, and the 1,5-AG level is hardly influenced by fluctuation during the course of a day or over several days. In general, a male tends to have a level of 1,5-AG slightly higher than a female. The cutoff value is about 14.0 µg/ml, where 95% of healthy people are diagnosed as "normal".

As a method of determining 1,5-AG, a gas chromatography method or an enzymatic method has been conventionally used, as described in Non-patent document 1. In the enzymatic method, 0.2 ml of a test sample of blood plasma (blood serum) is subjected to a protein removal treatment, and then, the content thereof is subjected to a mini-column to further remove contaminants included therein. Subsequently, the sample is treated with a pyranose oxidase (hereinafter, referred to as "PROD"). Then, hydrogen peroxide produced by the oxidation reaction of the hydroxyl group at the C2 position of 1,5-AG is stained by use of horseradish peroxidase (HRP), and the absorbance is measured at 420 nm Such a technique can be mentioned as an example of the enzymatic method. A determination kit specific to blood samples using such an enzymatic method has been developed.

Non-patent Document 1: Atsuo KAWAI and Yasuo AKANUMA, "1,5-anhydroglucitol", "Rinsyo-Kensa", vol. 33, No. 8, 1989 August, pp. 901-907.

Non-patent Document 2: "Medical Technology" (an extra edition), 2002, Vol. 30, No. 13, "All about diabetes testing— Screening to Testing for Complication", pp. 1498-1499 (Ishiyaku Pub, Inc.).

SUMMARY OF THE INVENTION

Problems to be Solved by the Invention

However, since a PROD, which is used in 1,5-AG determination according to conventional enzymatic methods, has a strong effect on glucose, there is a problem wherein it is required that a large amount of glucose present in blood (e.g. blood glucose) be removed so as to enable highly accurate 1,5-AG determination.

If a 1,5-AG-oxidizing enzyme (including oxidase and dehydrogenase), which has a low effect on glucose, is used instead of PROD, 1,5-AG determination could be simpler, the determination accuracy could be improved, or the determination time could be made shorter. Therefore, development of a method of determining 1,5-AG using such an enzyme has been sought.

The present invention was achieved under the above-described circumstances. That is, an object of the present invention is to provide a method of determining 1,5-AG and a reagent composition for determining 1,5-AG that are less affected by interfering substances and that can achieve 1,5-AG determination with a degree of accuracy higher than the prior-art method.

Means for Solving the Problems

In order to achieve the above-mentioned object, the present invention provides the following aspects.

[1] A method of determining 1,5-anhydroglucitol, including using (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% with the amino acid sequence of SEQ ID NO: 2 and which has sorbose dehydrogenase activity.

[2] The method of determining 1,5-anhydroglucitol according to [1], wherein the protein is derived from a bacterium that belongs to the genus *Sinorhizobium*.

[3] The method of determining 1,5-anhydroglucitol according to [1] or [2], wherein the protein is derived from *Sinorhizobium* sp. 97507 (Accession No. FERM BP-10843).

[4] The method of determining 1,5-anhydroglucitol according to any one of [1] to [3], wherein, assuming that the reactivity of the protein to sorbose is 100%, the reactivity of the protein to 1,5-anhydroglucitol is 10% or higher.

[5] The method of determining 1,5-anhydroglucitol according to any one of [1] to [4], wherein, assuming that the reactivity of the protein to 1,5-anhydroglucitol is 100%, the reactivity of the protein to D-glucose is 10% or less.

[6] The method of determining 1,5-anhydroglucitol according to any one of [1] to [5], wherein 1,5-anhydroglucitol included in a sample is affected by the protein in the presence of a chromogenic substrate, and the amount of reacted chromogenic substrate is measured.

[7] The method of determining 1,5-anhydroglucitol according to any one of [1] to [6], wherein D-glucose in a sample is removed before 1,5-anhydroglucitol included in a sample is affected by the protein.

[8] The method of determining 1,5-anhydroglucitol according to any one of [1] to [7], wherein 1,5-anhydroglucitol included in a sample is affected in the presence of a chromogenic substrate and an electron carrier.

[9] The method of determining 1,5-anhydroglucitol according to any one of [1] to [8], wherein 1 to 500 units of the protein is added to 1 mL of a sample where the enzyme activity of the protein measured using 1,5-anhydroglucitol as a substrate is defined as the base unit.

[10] The method of determining 1,5-anhydroglucitol according to any one of [1] to [9], wherein the protein is activated with an electron carrier before 1,5-anhydroglucitol included in a sample is affected by the protein.

[11] A reagent composition for determining 1,5-anhydroglucitol, including (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% with the amino acid sequence of SEQ ID NO: 2 and which has sorbose dehydrogenase activity.

[12] The reagent composition for determining 1,5-anhydroglucitol according to [11], wherein the protein is derived from a bacterium that belongs to the genus *Sinorhizobium*.

[13] The reagent composition for determining 1,5-anhydroglucitol according to [11] or [12], wherein the protein is derived from *Sinorhizobium* sp. 97507 (Accession No. FERM BP-10843).

[14] The reagent composition for determining 1,5-anhydroglucitol according to any one of [11] to [13], wherein, assuming that the reactivity of the protein to sorbose is 100%, the reactivity of the protein to 1,5-anhydroglucitol is 10% or higher.

[15] The reagent composition for determining 1,5-anhydroglucitol according to any one of [11] to [14], wherein, assuming that the reactivity of the protein to 1,5-anhydroglucitol is 100%, the reactivity of the protein to D-glucose is 10% or less.

[16] The reagent composition for determining 1,5-anhydroglucitol according to any one of [11] to [15], wherein the protein is activated with an electron carrier.

[17] The reagent composition for determining 1,5-anhydroglucitol according to [16], wherein the electron carrier is at least one of phenazine methosulfate and 1-methoxy-5-methylphenazinium methyl sulfate.

[18] The reagent composition for determining 1,5-anhydroglucitol according to any one of [11] to [17], further including a chromogenic substrate.

[19] The reagent composition for determining 1,5-anhydroglucitol according to [18], further including an electron carrier, wherein the chromogenic substrate is a reductive chromogenic substrate.

[20] A (a) protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has reactivity of 10% or higher to 1,5-anhydroglucitol, assuming that the reactivity of the protein to sorbose is 100%; or (c) a protein which consists of an amino acid sequence having a homology of at least 85% with the amino acid sequence of SEQ ID NO: 2 and which has activity of 10% or higher to 1,5-anhydroglucitol, assuming that the reactivity of the protein to sorbose is 100%.

[21] A method of diagnosing diabetes, including using the reagent composition for determining 1,5-anhydroglucitol according to any one of [11] to [19].

[22] Use of the reagent composition for determining 1,5-anhydroglucitol according to any one of [11] to [19] for determining 1,5-anhydroglucitol.

[23] Use of (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% with the amino acid sequence of SEQ ID NO: 2 and which has sorbose dehydrogenase activity, for determining 1,5-anhydroglucitol.

Effects of the Invention

The present invention can provide a method of determining 1,5-AG and a reagent composition for determining 1,5-AG that are less affected by interfering substances and that can achieve 1,5-AG determination with a degree of accuracy higher than the prior-art method.

Moreover, the method of determining 1,5-AG and a reagent composition for determining 1,5-AG and the reagent composition for determining 1,5-AG of the present invention can be applied to a clinical sample such as blood plasma, serum, cerebrospinal fluid or urine, and 1,5-AG included in such samples can be quickly and simply quantified or detected. Furthermore, small-scale measurement can be achieved in the present invention, and the present invention can achieve highly accurate and sensitive detection or quantification of 1,5-AG in an automatic biochemical-examination analyzing apparatus or the like that is generally used in clinical laboratory tests.

BEST MODE FOR CARRYING OUT THE INVENTION

Figure 1:
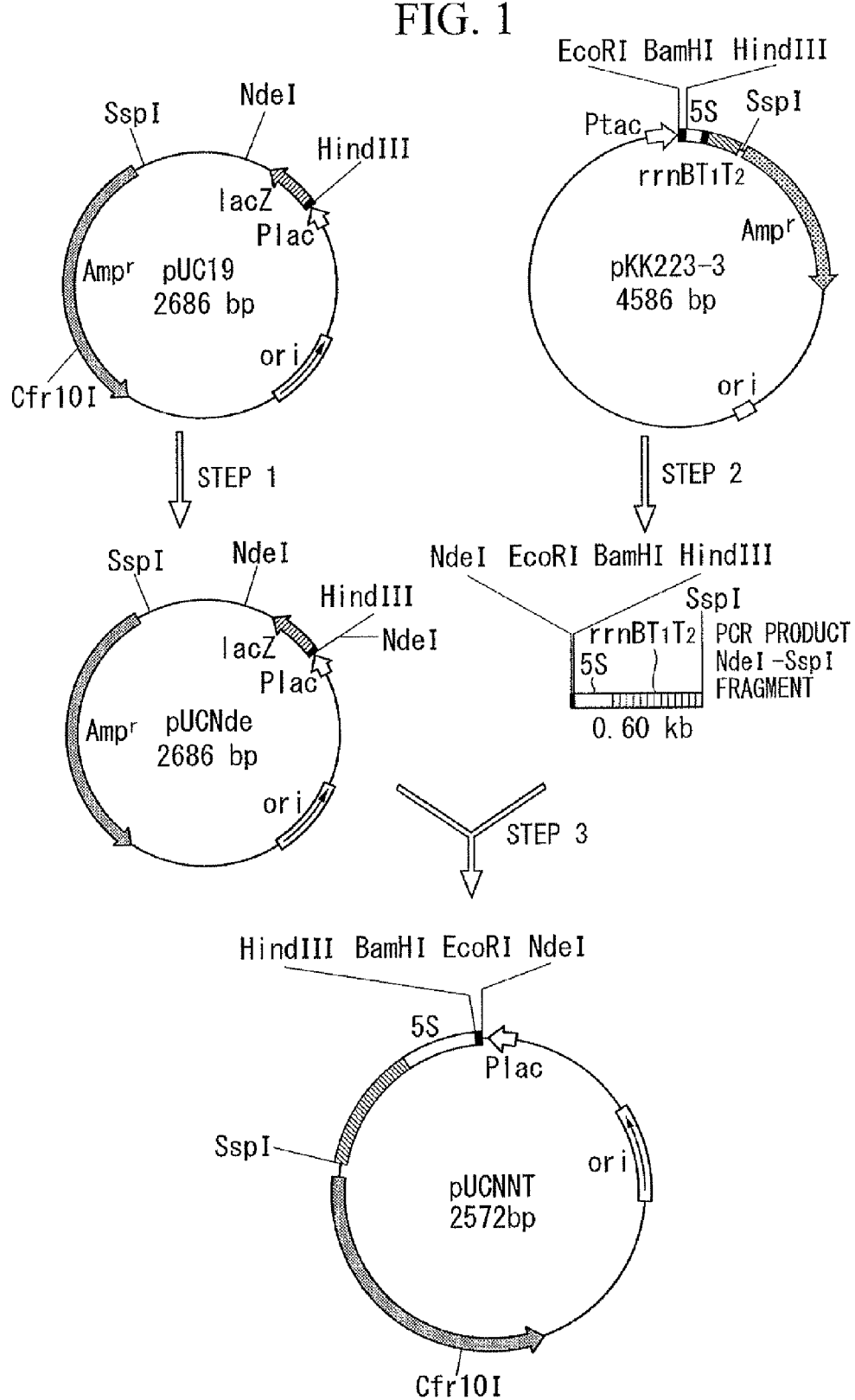
FIG. 1 is a schematic diagram that illustrates a first set of procedures for constructing a plasmid "pUCNNT2" used in production of a sorbose dehydrogenase in Example 1.

The method of determining 1,5-AG according to the present invention utilizes (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% with the amino acid sequence of SEQ ID NO: 2 and which has sorbose dehydrogenase activity.

Hereinafter, the above-described protein is referred to as a sorbose dehydrogenase.

It is preferable that the sorbose dehydrogenase used in the determination method of the present invention have the following physicochemical properties.
(1) The optimal pH is about 8.0, whereas the sorbose dehydrogenase exhibits an activity of 50% or higher within a range of 6.3-9.1;
(2) With regard to the pH stability, the sorbose dehydrogenase is stable within a pH range of 5.9-8.6 after the protein is treated at 40° C. for fifteen minutes;
(3) The optimal temperature is around 60° C. in a buffer whose pH is 7.0;
(4) With regard to the temperature stability, the sorbose dehydrogenase exhibits remaining activity of 77% or higher after the protein is treated in a buffer, whose pH is 7.0, at 45° C. for ten minutes, and is stable at about 45° C. or less;
(5) With regard to the substrate specificity and the Km value, the sorbose dehydrogenase has a strong effect on 1,5-AG and L-sorbose as a substrate while the sorbose dehydrogenase has little or a weak effect on sugars such as D-galactose or D-glucose. The Km value thereof may be about 82.5 mM with respect to 1,5-AG while the Km value may be about 65.6 mM with respect to L-sorbose.
(6) With regard to the molecular weight and the subunit molecular weight, the total molecular weight is about 150 kDa or about 672 kDa while the subunit molecular weight is about 59.6 kDa.
(7) With regard to the inhibitor specificity, the sorbose dehydrogenase is remarkably inhibited with a heavy metal ion (e.g. $Mn^{2+}$, $Hg^{2+}$ or $Cu^{2+}$).
(8) The sorbose dehydrogenase has an effect on L-sorbose, thereby producing L-sorbosone.
(9) The coenzyme thereof is flavin adenine dinucleotide (FAD).

The sorbose dehydrogenase used in the determination method of the present invention is not particularly limited with regard to its origin, the production method, etc. as long as the sorbose dehydrogenase has features described in the present description. The sorbose dehydrogenase may be a natural protein, a protein expressed from a recombinant DNA by way of genetic engineering techniques, or a chemically-synthesized protein. In particular, the sorbose dehydrogenase may be preferably derived from a bacterium which belongs to the genus Sinorhizobium, more preferably derived from Sinorhizobium sp. 97507 (Accession No. FERM BP-10843) or Sinorhizobium meliloti (preferably Strain 1021), and most preferably derived from Sinorhizobium sp. 97507 (Accession No. FERM BP-10843).

The term "derived from", as described above, refers to a protein coded by a sorbose dehydrogenase gene of the above-mentioned bacteria. The protein may be those directly extracted from bacteria, those expressed by genetic engineering techniques, those chemically synthesized, etc. and the production method thereof is not particularly limited.

Hereinafter, an example of the production method using genetic engineering techniques for the sorbose dehydrogenase used in the determination method of the present invention will be described.
(DNA Extraction)

Bacterial cells of Sinorhizobium sp. 97507 (Accession No. FERM BP-10843) are subjected to sonication or enzymatic lysis treatment to digest the cell wall. Then, the DNA is extracted with phenol, etc., and the DNA is recovered by way of salt precipitation, ethanol precipitation or the like.
(PCR)

The above-extracted DNA which is derived from Sinorhizobium sp. 97507 (Accession No. FERM BP-10843) is used as a template, and a plurality of primers prepared based on the nucleotide sequence of a sorbose dehydrogenase gene is used to conduct a PCR whereby the sorbose dehydrogenase gene is amplified. The produced PCR product is purified by agarose electrophoresis or the like, and DNA of the sorbose dehydrogenase gene is extracted from the agarose gel.
(Preparation of Recombinant Vector)

The expression vector used for preparation of a recombinant vector may be selected optionally from those which produce an intact form of the expressed protein, those which produce an N-terminal or C-terminal histidine-tagged form thereof, or those which produce a form in which a maltose-binding protein or a GST peptide is fused to the N-terminal or C-terminal thereof. The expression vector and DNA of the sorbose dehydrogenase gene obtained by the above PCR may be digested with the same restriction enzymes such as Nco I or Hind III, and then, DNA of the enzyme gene is ligated to the expression vector to prepare the recombinant vector.

Additionally, commercially-available products may be used for the expression vector. However, a specific site of commercially-available plasmid vectors may be substituted to stabilize the expression vector, and such substituted plasmid vectors are preferably used.

As described above, the method of determining 1,5-AG according to the present invention utilizes (a) a protein which consists of the amino acid sequence of SEQ ID NO: 2; (b) a protein which consists of an amino acid sequence having deletion, substitution and/or addition of one or more amino acid residues in the amino acid sequence of SEQ ID NO: 2 and which has sorbose dehydrogenase activity; or (c) a protein which consists of an amino acid sequence having a homology of at least 60% (60% to 100%) with the amino acid sequence of SEQ ID NO: 2 and which has sorbose dehydrogenase activity. However, the homology is preferably 65% or more (65% to 100%), more preferably 75% or more (75% to 100%), and most preferably 85% or more (85% to 100%).

In terms of the above-described homology of the amino acid sequence, manipulation of substitution, addition, deletion, etc. of an amino acid may be conducted with respect to the sorbose dehydrogenase-coding region inserted into the expression vector by way of site-specific mutagenesis using known base-substitution techniques such as the Kunkel method as long as the produced recombinant sorbose dehydrogenase can achieve the object of the present invention. Moreover, manipulation of substitution, addition, deletion, etc. of an amino acid may be conducted by way of random mutagenesis using known base-substitution techniques such as an error-prone PCR. Furthermore, a known technique such as DNA shuffling may be conducted with respect to sorbose dehydrogenase genes isolated from plural species of bacteria to produce a sorbose dehydrogenase having superior properties.

In addition, the term "homology" refers to a degree of identity between sequences of two or more genes. Accordingly, the higher the homology is between two types of genes, the higher the identity or similarity of the sequences. Whether two types of genes possess a homology can be evaluated by direct comparison of the sequences, or by a hybridization technique under stringent conditions for comparison between nucleotide sequences.

(Preparation of Transformant)

Introduction (e.g. transformation or transfection) of the recombinant vector including the sorbose dehydrogenase gene into a host cell can be achieved by conventional known techniques. For example, a method of Cohen et al. (Proc. Natl. Acad. Sci. USA., vol. 69, p. 2110, 1972), a protoplast method (Mol. Gen. Genet., vol. 168, p. 111, 1979) or a competent method (Journal of Molecular Biology, vol. 56, p 209, 1971) may be adopted to transform a bacterial host (*E. coli, Bacillus subtilis*, etc.); a method of Hinnen et al. (Proc. Natl. Acad. USA., vol. 75, p 1927, 1978) or a lithium method (J. Bacteriol., vol. 153, p. 163, 1983) may be adopted to transform yeasts (*Saccharomyces cerevisiae, Pichia pastoris*, etc.); a method of Graham (Virology, vol. 52, p 456, 1973) may be adopted to transform animal cells; and a method of Summers et al. (Mol. Cell. Biol., vol. 3, pp. 2156-2165, 1983) may be adopted to transform insect cells. Additionally, in the transformation, it is not always required to express the protein from the recombinant vector. For example, the following technique may be adopted. That is, the sorbose dehydrogenase gene used in the present invention may be inserted directly into the chromosome DNA of host cells to express the gene. Bacteria or yeasts are preferably used as hosts in the present invention since these host cells are easily handled and can produce a large amount of recombinant protein in a relatively short time. In particular, a microorganism that belongs to the genus *Escherichia* is more preferably used as the host.

(Expression and Harvest of Sorbose Dehydrogenase)

Transformant cells harboring the above-prepared expression vector are cultured in a nutrient culture medium and the expressed sorbose dehydrogenase is harvested to obtain the sorbose dehydrogenase used in the determination method of the present invention. The nutrient culture medium preferably contains a carbon source, or an inorganic or organic nitrogen source required for growth of the host cells. Examples of the carbon source include glucose, dextran, soluble starch, sucrose, or methanol. Examples of the inorganic or organic nitrogen source include ammonium salts, nitrates, amino acids, corn steep liquor, peptone, casein, meat extracts, soybean cake, or potato extracts. Additionally, the nutrient culture medium may optionally contain extra nutrients (e.g. inorganic salts such as sodium chloride, calcium chloride, sodium dihydrogen phosphate or magnesium chloride; vitamins; or antibiotics such as tetracycline, neomycin, ampicillin or kanamycin). Culturing can be achieved by methods known in the art. Culturing conditions such as the culturing temperature, pH of the medium or culturing time can be suitably selected so as to produce a large quantity of the sorbose dehydrogenase.

Host cells (i.e. transformants) such as microorganisms in which the sorbose dehydrogenase is expressed, as described above, can be recovered from the culture medium by a procedure such as centrifugation. The recovered host cells are suspended in a typical appropriate buffer solution. Then, the suspended host cells are subjected to mechanical treatment such as sonication, or enzymatic treatment such as lysozyme treatment. Furthermore, typical known purification techniques such as affinity chromatography, ion-exchange chromatography or gel filtration chromatography can be combined suitably to purify the sorbose dehydrogenase.

As described above, the sorbose dehydrogenase used in the present invention requires flavin adenine dinucleotide (FAD) as a coenzyme. However, if the sorbose dehydrogenase is produced under the aforementioned general conditions, a sorbose dehydrogenase which the coenzyme is bound to can be prepared without external addition of FAD.

Accordingly, it is not always required to artificially add FAD in the above-described production process, in the method of determining 1,5-AG or to the reagent composition for determining 1,5-AG of the present invention.

(Method of Activating Sorbose Dehydrogenase)

The sorbose dehydrogenase of the present invention can be activated if the sorbose dehydrogenase is incubated in the presence of an electron carrier. Therefore, prior to the determination method or production of the reagent composition for determining 1,5-AG of the present invention, the sorbose dehydrogenase may be subjected to such activation treatment. In particular, if the determination method or the reagent composition of the present invention is applied to clinical samples such as blood, it is preferable that the sorbose dehydrogenase be subjected to the activation treatment in advance. This is because highly sensitive detection of 1,5-AG can be achieved.

Examples of the electron carriers used for activation include phenazine methosulfate (PMS), 1-methoxy-5-methylphenazinium methyl sulfate (1m-PMS), etc. When 1m-PMS is used, the compound may be added to the prepared sorbose dehydrogenase in a final concentration of 0.01 mM to 50 mM, and more preferably in a final concentration of 0.01 mM to 10 mM, and the sorbose dehydrogenase is incubated therein at pH 5-9 at 4-45° C. for thirty minutes to one day. If an excessive amount of 1m-PMS remains therein after the activation treatment to prepare a measurement reagent, the excessive 1m-PMS can be removed by way of dialysis, ultrafiltration, etc. to apply the sorbose dehydrogenase to the determination method or the reagent composition for determining 1,5-AG of the present invention.

The sorbose dehydrogenase used in the present invention can be activated by the above-mentioned treatment. The enzyme activity after the activation treatment, which is measured with 1,5-AG as the substrate thereof, as described below, is activated preferably two times (2-20 folds) higher, and more preferably four times (4-10 folds) higher than before the activation treatment.

(Determination Method)

According to the method of determining 1,5-AG of the present invention, the quantity of 1,5-AG in a sample such as blood or cerebrospinal fluid can be precisely determined. As described above, the 1,5-AG level in blood is useful as a control marker for diabetes. Accordingly, the determination method of the present invention is useful for diagnosis of diabetes.

The method of determining 1,5-AG of the present invention may be conducted, for example, by the following procedures. The sorbose dehydrogenase may be added to 1 mL of a body fluid sample, which is expected to contain 1,5-AG, in a final concentration of 1 to 500 units where the enzyme activity measured using 1,5-AG as a substrate is defined as the base unit. Furthermore, when using a chromogenic substrate which reacts directly due to the sorbose dehydrogenase of the present invention, only the chromogenic substrate may be added thereto. When using a chromogenic substrate which does not react directly due to the sorbose dehydrogenase of the present invention but which develops a color by reduction in the presence of an electron carrier; or a chromogenic substrate which slightly develops a color due to the sorbose dehydrogenase of the present invention but which remarkably develops a color by reduction in the presence of an electron carrier, an electron carrier may be added thereto besides the chromogenic substrate. While the sample is incubated preferably at 4° C. to 50° C. (more preferably at 25° C. to 40° C.) for one minute to three hours (more preferably for one minute to thirty minutes, and most preferably for one minute to ten minutes), changes in the absorbance are measured. Based on a standard curve formulated in advance, the concentration of 1,5-AG in the sample is determined.

In addition, a "chromogenic substrate" includes the chromogenic substrate which reacts directly due to the dehydrogenase; the chromogenic substrate which develops a color by reduction in the present of an electron carrier; and the chromogenic substrate which remarkably develops a color by reduction in the presence of an electron carrier, as described above. Furthermore, a "reductive chromogenic substrate" include the chromogenic substrate which develops a color by reduction in the present of an electron carrier; and the chromogenic substrate which remarkably develops a color by reduction in the presence of an electron carrier, as described above.

The sorbose dehydrogenase used in the method of determining 1,5-AG of the present invention at least needs to react with 1,5-AG to such an extent that the dehydrogenase can stand up to practical use. Sorbose is a sugar which does not exist in a living body. Therefore, the reactivity with sorbose is not particularly a matter. However, with regard to the reactivity of the sorbose dehydrogenase to 1,5-AG, a sorbose dehydrogenase having a reactivity of preferably 10% or higher (10% to 200%), more preferably 50% or higher (50% to 200%) can be used where the reactivity to sorbose is considered as 100% although it depends on a test samples. Furthermore, with regard to the sorbose dehydrogenase used in the method of determining 1,5-AG of the present invention, a sorbose dehydrogenase having little or a weak effect on D-glucose may be used. Since a large amount of D-glucose is present in a test sample, a sorbose dehydrogenase having a reactivity to D-glucose of preferably 10% or less (0.001% to 10%), and more preferably 5% or less (0.001% to 5%) may be selected whereby the requirement and stringency of pretreatment to the sample (in particular, treatment of removing sugars such as D-glucose) can be substantially reduced. Consequently, facilitation of the measurement, reduction in the measurement time, improvements in the measurement accuracy and cost reduction can be achieved.

In addition, the above-mentioned "reactivity" is reactivity evaluated based on the maximum reaction rate of the enzyme that catalyzes the reaction with the substrate, i.e. sorbose, 1,5-AG or D-glucose where the excessive amount of substrate is affected by a certain amount of enzyme used in the reaction. As an example of "reactivity", the "method of measuring enzyme activity" (where sorbose is used), as described below, can be mentioned.

As described above, the sorbose dehydrogenase used in the method of determining 1,5-AG of the present invention has high specificity to 1,5-AG However, the sorbose dehydrogenase may be slightly influenced by D-glucose. For example, when the sorbose dehydrogenase is applied to samples of diabetics whose concentration of D-glucose reaches thousands of times the concentration of 1,5-AG, the influence of D-glucose may be nonnegligible. When dealing with such samples, a D-glucose-removing agent or D-glucose-eliminating agent may be added to completely prevent the influence of D-glucose. That is, it is required to determine 1,5-AG after the influence of D-glucose is eliminated in advance by addition of such a D-glucose-removing or eliminating agent.

As an example of a method of removing sugars such as D-glucose, a method using an ion-exchange resin, as disclosed in Japanese Patent Publication No. H5-41235, can be mentioned. As a method of eliminating D-glucose, a method of converting D-glucose to glucose-6-phosphate using an enzyme phosphorylating glucose at C6 (hexokinase or glucokinase) can be applied to the present invention, as disclosed in Japanese Patent Publication No. H1-320998, Japanese Examined Patent Application, Second Publication No. H7-71514, Japanese Patent Publication No. H6-237795, Japanese Patent Publication No. H3-27299, Japanese Patent Publication No. H6-245796, Japanese Examined Patent Application, Second Publication No. H7-102154, etc. The second method of eliminating D-glucose may be preferably adopted because the samples can be set in a general automatic measurement apparatus for a biochemical examination. In this case, it is preferable that glucokinase, which has high specificity to D-glucose, be used as the enzyme phosphorylating glucose at C6. Although the amount of glucokinase varies with the amount of glucose in the sample, the amount of glucokinase may be 1 U/mL to 20 U/mL. Moreover, although the amount of adenosine triphosphate (ATP) required for phosphorylation of glucose varies with the amount of glucose in the sample, the amount of ATP may be 0.5 mM to 20 mM. Additionally, 2 mM to 50 mM of magnesium chloride may be added to promote the phosphorylation of D-glucose.

Furthermore, if a higher level of elimination of D-glucose is required, for example, the above-mentioned D-glucose-6-phosphorylation system using glucokinase can be combined with an enzyme-cycling system, e.g. an ATP-cycling system using pyruvate kinase, thereby achieving complete elimination of D-glucose.

With regard to the chromogenic substrate which reacts directly due to the sorbose dehydrogenase of the present invention, for example, an electron acceptor such as 2,6-dichlorophenol indophenol (DCIP) can be mentioned.

Moreover, a ferricyanide compound such as potassium ferricyanide may be used as an electron acceptor, and changes in the color development of the electron acceptor may be detected after the oxidation-reduction reaction by the sorbose dehydrogenase. Otherwise, a method wherein a ferric sulfate-dupanol reagent is added, and this is color-developed as Prussian blue can be applied. However, in terms of ease and detection sensitivity, chromogenic substrates such as DCIP that react directly due to the sorbose dehydrogenase, thereby enabling highly sensitive measurement, may be preferably used.

With regard to the chromogenic substrates which develop a color by reduction in the presence of an electron carrier or which remarkably develop a color by reduction in the presence of an electron carrier, tetrazolium or salts thereof may be used. Typical examples thereof include nitrotetrazolium blue (NTB); 2-(4-iodophenyl)-3-(4-nitrophenyl)-5-phenyl-2H-tetrazolium chloride; 3-(4,5-dimethyl-2-thiazolyl)-2,5-diphenyl-2H-tetrazolium bromide; 2-(4-iodophenyl)-3-(4-nitrophenyl)-5-(2,4-disulfophenyl)-2H-tetrazolium, monosodium salt (WST-1); 2-(4-iodophenyl)-3-(2,4-dinitrophenyl)-5-(2,4-disulfophenyl)-2H-tetrazolium, monosodium salt (WST-3); or 2-(2-methoxyl-4-nitrophenyl)-3-(4-nitrophenyl)-5-(2,4-disulfophenyl)-2H-tetrazolium, monosodium salt (WST-8). The concentration thereof may be within a range of 0.05 mM to 4 mM, and preferably within a range of 0.1 mM to 2 mM.

With regard to the electron carrier used for the color development of tetrazoliums or salts thereof, phenazine methosulfate (PMS), 1-methoxy-5-methylphenazinium methyl sulfate (1m-PMS), etc. can be mentioned. When using 1m-PMS, the concentration thereof may be within a range of 0.01 mM to 50 mM, and more preferably within a range of 0.01 mM to 10 mM.

With regard to a buffer used in the above-described determination method, any generally-used buffer such as a phosphate buffer, Tris-HCl buffer, Good's buffer, or boric acid buffer can be used (pH 6-10).

(Reagent Composition for Determination)

The reagent composition for determining 1,5-AG of the present invention contains the above-described sorbose dehydrogenase as an essential component, and is useful for diagnosis of diabetes. The form of reagent can be modified suitably according to objective samples, a chromogenic agent used therein, a mode of measurement, among others.

For example, the reagent composition for determining 1,5-AG of the present invention may be combined with a reagent that eliminates sugars such as D-glucose (sugar-eliminating agent), as described above, when applying the reagent composition to measurement of samples derived from diabetes, containing a high concentration of D-glucose. As such a sugar-eliminating agent, the above-described known techniques can be adopted. Combination of a borate-bound resin, anion-exchange resin and cation-exchange resin, or combination of a strong basic anion-exchange resin and cation-exchange resin is preferable. When a sample is treated with a strong basic anion-exchange resin or boric acid, 1,5-AG is not removed, but sugars are selectively removed, thereby obtaining a sample containing 1,5-AG Furthermore, an enzyme that does not have effects on 1,5-AG but that has effects on other sugars can be used to remove sugars other than 1,5-AG Examples of such an enzyme include a hexokinase or glucokinase, as described above. Glucose can be phosphorylated by using such enzymes, thereby removing glucose. Additionally, a method of removing D-glucose in a sample using a glucose oxidase can be mentioned. The reaction product from D-glucose by a glucose oxidase is D-glucono-1,5-lactone.

The reagent composition for determining 1,5-AG may be prepared in a form of a single reagent obtained by mixing all components, or may be divided in appropriate combination of components if components interfere with each other. The reagent composition may be prepared into a liquid or powdery reagent. Furthermore, the reagent composition may be included in a support such as filter paper or films whereby the reagent composition can be prepared as a test paper or analytical film. Additionally, a protein-removing agent such as perchloric acid, or a standard reagent containing 1,5-AG may be attached to the reagent composition for determining 1,5-AG With regard to the amount of enzyme (sorbose dehydrogenase) included in the reagent composition, it is preferable that the reagent composition be prepared such that the final concentration thereof is about 0.1 units/mL to 50 units/mL in a reaction solution with respect to one sample where the enzyme activity measured using 1,5-AG as a substrate is defined as the base unit. As examples of samples for the 1,5-AG quantification, blood plasma, serum, cerebrospinal fluid, or urine can be mentioned.

With regard to application of the reagent composition for determining 1,5-AG of the present invention, application to a large-size universal automatic measurement machine for biochemical examination can be considered as the most common use. However, a small-sized specialized machine or a portable machine for general practitioners can be considered.

When a reagent composition for determining 1,5-AG used for such automatic measurement machines is prepared, for example, addition of a reductive color-producing agent (a tetrazolium and an electron carrier when the reductive color-producing agent is a tetrazolium) and a sorbose dehydrogenase to a sample can be conducted at the same time except that a D-glucose-eliminating agent needs to be added in advance. That is, the components other than the D-glucose-eliminating agent may be prepared into one reagent. Furthermore, if, among a D-glucose-eliminating agent, tetrazolium, electron carrier, and sorbose dehydrogenase, there are some components that interfere with each other, the components may be prepared, for example, into separate reagents to prevent such interference.

Hereinafter, the present invention will be described in detail with respect to Examples. However, the present invention is not limited to Examples below.

EXAMPLES

Example 1

Identification of a Bacterium to Use

The bacterium used in the experiment was isolated from root nodules of alfalfa, and bacteriological properties of the bacterium were as follows.

1. Morphological properties

The morphological properties of the bacterium grown in a yeast extract-mannitol medium are described below. The morphology of bacterial cells was rod-shaped, and the size was 0.5-0.9 μm×1.2-3.0 μm. The bacterium did not form a spore, and Gram staining was negative.

2. Growth State on a Culture Medium

The growth state of the bacterium grown in a yeast extract-mannitol medium is described below. The colonies exhibited as cream-white, the morphology thereof was circular and swollen, being gibbous-shaped, and the colonies were viscous. Colonies grown at 30° C. for three days had a diameter of 2-4 mm. Additionally, the bacterium had flagella and motility.

3. Physiological Properties.

The bacterium was aerobic and the optimal growth temperature was 25-30° C., and the optimal growth pH was 6-8. The consumption of typical sugars is shown in Table 2. The bacterium produced oxidase and catalase.

TABLE 2

| | |
|---|---|
| D-arabinose | + |
| Cellobiose | + |
| Fructose | + |
| D-galactose | + |
| Glucose | + |
| Lactose | + |
| D-mannose | + |
| Mannitol | + |
| D-ribose | + |
| Xylose | + |
| Cellulose | − |
| Sorbose | − |
| Dulcitol | − |
| Fucose | − |

The genus which the bacterium belonged to was determined based on the above-described isolated source and properties in accordance with "Bergey's Manual of DETER- MINATIVE BACTERIOLOGY (9$^{TH}$ edition)". Consequently, it was discovered that the bacterium was a microorganism that belonged to the genus *Sinorhizobium*. The bacterium was designated as *Sinorhizobium* sp. 97507. *Sinorhizobium* sp. 97507 was deposited at the International Patent Organism Depositary, National Institute of Advanced Industrial Science and Technology by the present applicant(s) on Jul. 10, 2003, and accession No. FERM P-19428 (Japanese national deposit) was obtained on a receipt dated Jul. 11, 2003 issued by the International Patent Organism Depositary. Hereinafter, *Sinorhizobium* sp. 97507 (FERM P-19428) is referred to as a "deposited strain".

Furthermore, the present applicant(s) filed a request for transferring the above-mentioned *Sinorhizobium* sp. 97507 (original deposit; national accession No. FERM P-19428) to an international deposit at the International Patent Organism Depositary, National Institute of Advanced Industrial Science and Technology (international depositary authority) on Jun. 22, 2007, and the petition was received by the international depositary authority on the same day. Receipt No. FERM ABP-10843 was issued on the receipt of the request.

[Cloning of Sorbose Dehydrogenase]

A genomic DNA was extracted from the deposited strain, and a sorbose dehydrogenase was cloned by the following procedures.

1. Extraction of Genomic DNA

The bacterial cells of the deposited strain were treated with lysozyme to digest the cell wall. Then, the DNA was extracted with phenol, and the DNA was purified by salt precipitation, and recovered.

2. PCR

PCR was conducted under the following conditions, and the PCR product including a sorbose dehydrogenase gene of about 1.6 kbp was obtained.

Template: DNA extracted in 1. (derived from the deposited strain).

Primers: DNAs represented by SEQ ID NO: 3 and SEQ ID NO: 4.

(Primers 1 and 2 were designed based on a nucleotide sequence "SMa1414" (putative L-sorbose dehydrogenase) disclosed by *Sinorhizobium meliloti* strain 1021 Genome Project (web site: http://sequence.toulouse.inra.fr/meliloti.html).)

Polymerase: TaKaRa LA Taq (manufactured by Takara Bio Inc.)

Reaction Conditions:
a. Denaturation at 94° C. for one minute (one cycle)
b. Denaturation at 94° C. for thirty seconds
c. Annealing at 57° C. for one minute
d. Extension reaction at 72° C. for two minutes
e. Extension reaction at 72° C. for five minutes (one cycle)
30 cycles of the reactions of b to d were conducted.

3. Purification of the Product from the Excised Gel.

The PCR product obtained in 2. was subjected to agarose gel electrophoresis to purify the product. The DNA of the sorbose dehydrogenase gene was extracted from the agarose gel by using "QIAEXII Gel Extraction Kit" (manufactured by Qiagen).

4. Treatment with Restriction Enzyme

The DNA of the sorbose dehydrogenase gene extracted and purified from the agarose gel in 3. and plasmid "pUCNNT2" were treated with restriction enzymes NcoI and HindIII. The DNA of the sorbose dehydrogenase gene and plasmid pUCNNT2 treated with restriction enzymes were purified by agarose gel electrophoresis, and were extracted from the agarose gel by using "QIAEXII Gel Extraction Kit" (manufactured by Qiagen).

Figure 2:
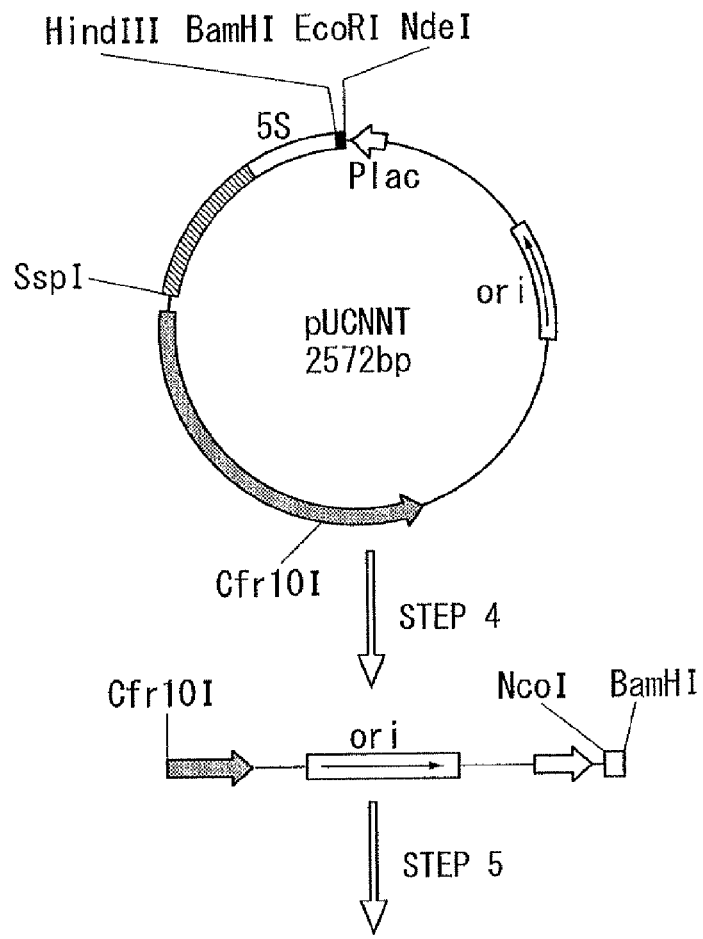
FIG. 2 is a schematic diagram that illustrates a second set of procedures mentioned in FIG. 1.
Figure 2:
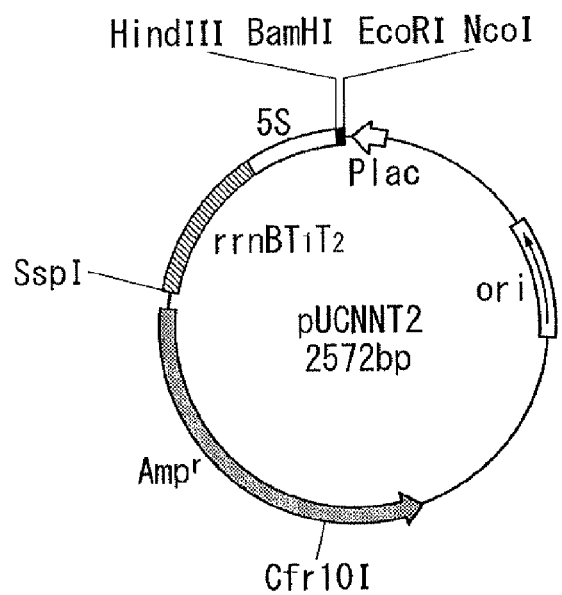

In addition, the plasmid pUCNNT2 was a plasmid prepared by inserting, to a commercially-available plasmid pUC19 (manufactured by Takara Bio Inc.), an NcoI linker and an rrnB ribosomal terminator derived from pKK223-3 (manufactured by Pharmacia Biotech) that contributes to stabilization of a plasmid, and was particularly suitable for expression of the sorbose dehydrogenase used in the present invention. FIGS. 1 and 2 are flowcharts that illustrate construction of the plasmid pUCNNT2 used in the present Example. As shown in FIGS. 1 and 2, the plasmid pUCNNT2 was constructed by the following steps 1-5.

Step 1: "pUCNde" was prepared by adding an NdeI linker to a commercially-available plasmid pUC19 (manufactured by Takara Bio Inc.).

Step 2: the EcoRI-SspI region of pKK223-3 (manufactured by Pharmacia Biotech) was amplified by a PCR. In this case, an NdeI linker was inserted (i.e. NdeI-SspI fragment of a PCR product).

The rrnBT$_1$T$_2$ in the NdeI-SspI fragment of the PCR product shown in FIG. 1 contributes to stability of a plasmid.

Step 3: the NdeI-SspI region of pUCNde was substituted with NdeI-SspI fragment of the PCR product to prepare a plasmid pUCNNT.

Step 4: the Cfr10I-BamHI region of pUCNNT was amplified by a PCR. In this case, the NdeI linker was converted to an NcoI linker.

Step 5: the Cfr10I-BamHI region of pUCNNT was substituted with the amplified fragment to prepare plasmid pUCNNT2.

5. Ligation

The DNA of sorbose dehydrogenase gene and plasmid pUCNNT2 treated with restriction enzymes in 4. were ligated with DNA Ligation Kit Ver. 2.1 (manufactured by Takara Bio Inc.) to construct plasmid pUCNNT2_AGD1.

6. Transformation

*E. coli* JM109 competent cells (manufactured by Takara Bio Inc.) were transformed with plasmid pUCNNT2_AGD1 constructed in 5. The transformed competent cells were inoculated on an LB plate containing ampicillin sodium, and cultured at 37° C. overnight. With respect to twenty colonies grown on the LB plate containing ampicillin sodium, it was confirmed by a direct PCR whether the plasmid including the sorbose dehydrogenase gene was introduced thereto. Consequently, seven isolates where amplification of the sorbose dehydrogenase gene was confirmed were inoculated on LB plates containing ampicillin sodium, and purified.

7. Confirmation of Activity.

(1) the purified seven isolates of gene-manipulated *E. coli* were cultured in liquid media under the following conditions.

Culture medium:
LB medium 10 mL
Bacto Tryptone (manufactured by Becton, Dickinson and Co.) 1.00% (w/v)
Bacto Yeast Extract (manufactured by Becton, Dickinson and Co.) 0.50% (w/v)
Sodium chloride (manufactured by Nacalai Tesque Inc.) 1.00% (w/v)
Ampicillin sodium (manufactured by Wako Pure Chemical Industries, Ltd.) 0.005% (w/v)

Culture container: a test tube (diameter 2.5 cm×length 20 cm)

Culture conditions: 37° C., fifteen hours, and 121 rpm (2) Bacterial cells were harvested from 10 mL of the culture medium (centrifuged at 1000×g for ten minutes at room temperature).

(3) The supernatant was removed, and the bacterial cells were suspended in 1 mL of a disruption buffer (50 mM KPB, pH 7.5; 0.25% (w/v) "BL-9EX" manufactured by Nikko Chemicals co., Ltd.; and 0.01% (w/v) flavin adenine dinucleotide (FAD)).

(4) The bacterial cells were disrupted with a tip-type sonication disruption apparatus (incubated in an ice bath for five minutes).

(5) The solution of disrupted bacterial cells was centrifuged at 13000×g at 4° C. for five minutes, and the supernatant (cell-free extract) was recovered. The cell-free extract was used as a sample for the activity measurement.

(6) The expression of activity was confirmed based on the "method of measuring enzyme activity" described below. The strain having the highest sorbose dehydrogenase activity was designated as "E. coli JM109/pUCNNT2_AGD1". In addition, the sorbose dehydrogenase activity/medium was 0.080 U/mL.

Then, the nucleotide sequence of the plasmid pUCNNT2_AGD1, which was extracted from the cultured bacterial cells of E. coli JM109/pUCNNT2_AGD1, was determined. It was confirmed that a DNA fragment coding the sorbose dehydrogenase was inserted therein. The nucleotide sequence is shown as SEQ ID NO: 1 while the amino acid sequence is shown as SEQ ID NO: 2.

Furthermore, the nucleotide sequence determined in the present example was compared with a putative sorbose dehydrogenase-coding region (locus tag: SMa1414) disclosed in the above-mentioned genome project of Sinorhizobium meliloti strain 1021. Consequently, the $160^{th}$ nucleotide was adenine (A) in SMa1414 while the corresponding nucleotide was cytosine (C) in the nucleotide sequence of the present example. Resulting from the nucleotide substitution, the $54^{th}$ amino acid was methionine (Met) in SMa1414 (Accession No.: NP_436019) while the corresponding amino acid was leucine (Leu) in the amino acid sequence of the present example.

[Production of Sorbose Dehydrogenase]

The gene recombinant (E. coli JM109/pUCNNT2_AGD1) harboring the sorbose dehydrogenase gene, as prepared above, was cultured, and the sorbose dehydrogenase was extracted and purified from the obtained bacterial cells.

In addition, the gene recombinant E. coli JM109/pUCNNT2_AGD1 was deposited at the International Patent Organism Depositary, National Institute of Advanced Industrial Science and Technology by the present applicant(s) in Mar. 28, 2006, and accession No. FERM P-20854 (Japanese national deposit) was obtained on a receipt dated Mar. 28, 2006 issued by the International Patent Organism Depositary.

1. Culturing

Bacterial cell: gene recombinant E. coli JM109/pUCNNT2_AGD1

1.1 Seed Culture

One L of LB medium was added to a 2.0 L shake flask, this was autoclaved at 121° C. for twenty minutes, and a filter-sterilized ampicillin sodium solution was added in a final concentration of 0.005% (w/v) immediately before use. The gene recombinant E. coli JM109/pUCNNT2_AGD1 was inoculated into the LB medium with a platinum loop, and cultured at 37° C. with shaking (120 rpm). The culture medium after culturing for thirteen hours was used as an inoculum for main culture.

Composition of LB Medium:
  Bacto Tryptone (manufactured by Becton, Dickinson and Co.) 1.00% (w/v)
  Bacto Yeast Extract (manufactured by Becton, Dickinson and Co.) 0.50% (w/v)
  Sodium chloride (manufactured by Nacalai Tesque Inc.) 1.00% (w/v)
  Ampicillin sodium (manufactured by Wako Pure Chemical Industries, Ltd.) 0.005% (w/v)

1.2 Main culture

Twenty one L of a GYC medium was charged to a 30 L culture apparatus, and autoclaved at 121° C. for twenty minutes. A filter-sterilized solution of ampicillin sodium (manufactured by Wako Pure Chemical Industries, Ltd.) and a filter-sterilized solution of isopropyl β-D-1-thiogalactopyranoside (manufactured by SIGMA-ALDRICH Japan K.K.) were added in a final concentration of 0.005% (w/v) and 0.024% (w/v), respectively, immediately before use.

Composition of the GYC Medium (adjusted to pH 7.0 with a 15 N NaOH Solution):
  glycerol (manufactured by Sakamoto Yakuhin Kogyo Co., Ltd.) 4.0% (w/v)
  Yeast Extract (manufactured by Ajinomoto Co., Inc.) 2.0% (w/v)
  Corn steep liquor (manufactured by San-ei Sucrochemical Co., Ltd.) 4.5% (w/v)

One L of the seed culture prepared in 1.1 was inoculated into the above medium, and cultured for fifteen hours under the following conditions. In addition, the medium was controlled at pH 7.0 with a 15 N NaOH solution while culturing.

Culturing temperature: 37° C.
Aeration: 1 v/v/m
Agitation speed: 350 rpm

Fifteen hours after culturing was started, 955.06 g of bacterial cells were harvested with a centrifuge.

2. Purification

The sorbose dehydrogenase was extracted and purified from bacterial cells obtained by culturing through the purification steps described below. The total activity, specific activity, yield, and specific activity ratio (fold) were measured. The results are shown in Table 3.

The sorbose dehydrogenase activity was measured based on the "method of measuring enzyme activity", as described below.

TABLE 3

| Purification step | Total activity (U) | Specific activity (U/mg) | Yield (%) | Fold |
|---|---|---|---|---|
| CFE | 3,318 | 0.24 | 100 | 1.00 |
| Ammonium sulfate pre. and dialysis | 2,894 | 0.918 | 87.2 | 3.82 |
| Strong anion-exchange chromatography (TOYOPEARL Super Q-650M) | 619 | 0.777 | 18.7 | 3.23 |
| Desalting and concentration | 798 | 1.05 | 24.0 | 4.35 |

2.1 Preparation of Cell-Free Extract (CFE)

With regard to 955.06 g of bacterial cells obtained in the main culture of 1.2, 200 g thereof was used to purify the sorbose dehydrogenase. 1 L of a disruption buffer (50 mM KPB, pH 7.5; 0.25% (w/v) BL-9EX (manufactured by Nikko Chemicals co., Ltd.); and 0.001 mM FAD) was added to 200 g of the bacterial cells to prepare a suspension of bacterial cells. Phenylmethylsulfonyl fluoride (PMSF), i.e. a serine protease inhibitor, was added to the suspension in a final concentration of 1 mM, and the bacterial cells were disrupted with a tip-type sonication disruption apparatus. The solution of the disrupted bacterial cells was centrifuged at 13000×g at 4° C. for fifteen minutes, and the supernatant was recovered. The supernatant was designated as CFE.

2.2 Ammonium Sulfate Fractionation

Ammonium sulfate was added to 1095 mL of CFE recovered in 2.1 in a final concentration of 40% (w/v) in an ice bath. In this case, the CFE was adjusted to pH 7.5 with ammonia. After ammonium sulfate was dissolved, the CFE was allowed to stand at 4° C. overnight.

2.3 Dialysis

The ammonium sulfate precipitate was recovered by centrifugation (13,000×g, 4° C. and 15 min) The recovered ammonium sulfate precipitate was put into a dialysis tube (seamless cellulose tube, small size 18, manufactured by Wako Pure Chemical Industries, Ltd.), and this was dialyzed with a dialysis buffer (5 mM KPB, pH 8.0; 0.25% (w/v) BL-9EX (manufactured by Nikko Chemicals Co., Ltd.); and 0.001 mM FAD).

2.4 Centrifugation

An insoluble matter was present inside the dialysis tube. Therefore, the insoluble matter was removed by centrifugation (13000×g, 4° C. and 15 mM), and the supernatant was recovered.

2.5 Strong Anion-Exchange Chromatography (TOYOPEARL Super Q-650M)

The supernatant recovered in 2.4 was charged to 350 mL (column size: φ 6.2 cm×height 27 cm) of a strong anion-exchange resin "TOYOPEARL Super Q-650M" (manufactured by Tosoh Corporation) equilibrated with an equilibration buffer (5 mM KPB, pH 8.0; 0.25% (w/v) BL-9EX (manufactured by Nikko Chemicals co., Ltd.); and 0.001 mM FAD). After charging, the resin was washed with five resin-bed volume of buffer (5 mM KPB, pH 8.0; 0.25% (w/v) BL-9EX (manufactured by Nikko Chemicals co., Ltd.); and 0.001 mM FAD) for washing. Then, the objective protein was gradient-eluted with two types of elution buffers (buffer 1: 5 mM KPB, pH 8.0, 0.25% (w/v) BL-9EX (manufactured by Nikko Chemicals Co., Ltd.), and 0.001 mM FAD; and buffer 2: 5 mM KPB, pH 8.0, 0.25% (w/v) BL-9EX (manufactured by Nikko Chemicals co., Ltd.), 0.001 mM FAD, and 1 M NaCl) (each volume was 2.5 times the bed volume of resin) to recover active fractions.

2.6 Desalting and Concentration

The active fractions obtained by the strong anion-exchange chromatography (TOYOPEARL Super Q-650M) of 2.5 were subjected to desalting and concentration treatment using an ultrafiltration equipment "Vivacell 250" (manufactured by Vivascience, molecular cutoff: 10,000). Finally, the buffer solution wherein the sorbose dehydrogenase was dissolved was substituted with a 50 mM KPB buffer, pH 7.5, containing 0.25% (w/v) BL-9EX (manufactured by Nikko Chemicals co., Ltd.), and 0.01 mM FAD, thereby obtaining the sorbose dehydrogenase.

[Method of Measuring Enzyme Activity]

One mL of a 0.1 M potassium phosphate buffer, pH 7.0, 1.0 mL of 1.0 M L-sorbose, 0.14 mL of 3 mM 2,6-dichlorophenol indophenol (DCIP), 0.2 mL of 3 mM 1-methoxy-5-methylphenazinium methyl sulfate, and 0.61 mL of water were added to a 3 mL quartz cell, and the quartz cell was set to a spectrophotometer equipped with a thermostat cell holder, and incubated at 37° C. for ten minutes. Then, 0.05 mL of the enzyme solution was added to the quartz cell, and changes in absorbance of DCIP at 600 nm (ΔABS600/min) was measured at 37° C. As the molar extinction coefficient of DCIP at pH 7.0 is known as 16.3 mM$^{-1}$, and the amount of enzyme that reduced 1 μmol of DCIP for one minute is defined as one unit. Following the definition, the concentration of enzyme activity was calculated based on the following equation.

$$\text{enzyme activity (units/mL)} = (-\Delta ABS600/\min \times 3.0 \times \text{dilution rate})/(16.3 \times 1.0 \times 0.05)$$

Optical path length: 1.0 cm

[Evaluation of Properties of Sorbose Dehydrogenase]

Measurement conditions in the above "method of measuring enzyme activity" were suitably modified as necessary, and the optimal pH, pH stability, optimal temperature, temperature stability, substrate specificity, Km value, total molecular weight, subunit molecular weight, inhibitor, and product of the enzyme reaction were identified. The properties of the enzyme were evaluated in accordance with the following tests.

Figure 3:
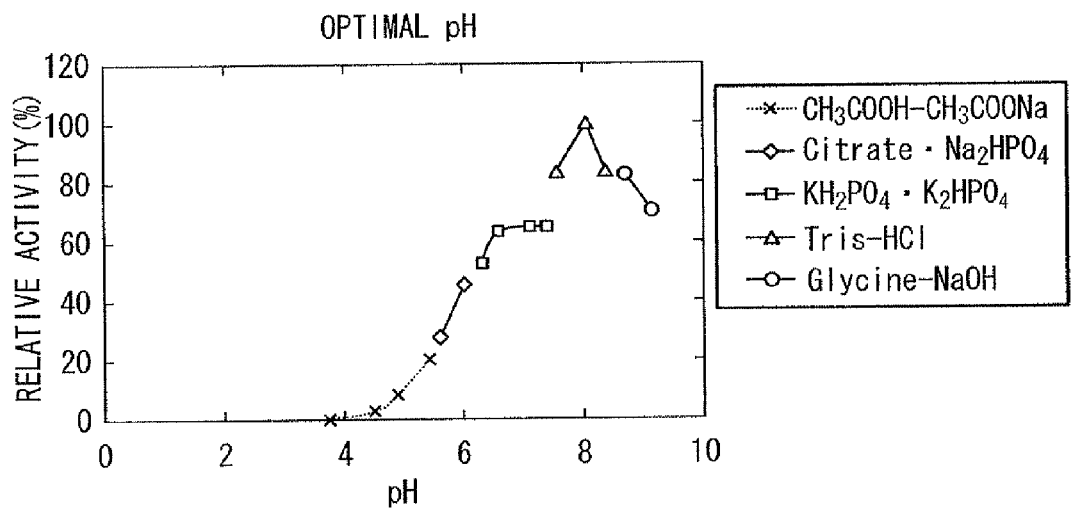
FIG. 3 is a graph showing measurement results of optimal pH for the sorbose dehydrogenase produced in Example 1.

(1) Optimal pH:

The buffer solution in the above "method of measuring enzyme activity" was substituted with an acetic acid-sodium acetate buffer (pH 3.71-5.36), a citric acid-sodium phosphate buffer (pH5.55-5.95), a potassium phosphate buffer (pH 6.25-7.35), a Tris-HCl buffer (pH 7.52-8.34), or a glycine-sodium hydroxide buffer (pH 8.68-9.11) (all buffers were adjusted to the final concentration of 33.3 mM) to determine the enzyme activity of the purified enzyme. In addition, the molar extinction coefficient of DCIP at each value of pH obtained in advance was used to calculate the enzyme activity. The results are shown in FIG. 3. As shown in FIG. 3, the optimal pH for the sorbose dehydrogenase was 8.0.

Figure 4:
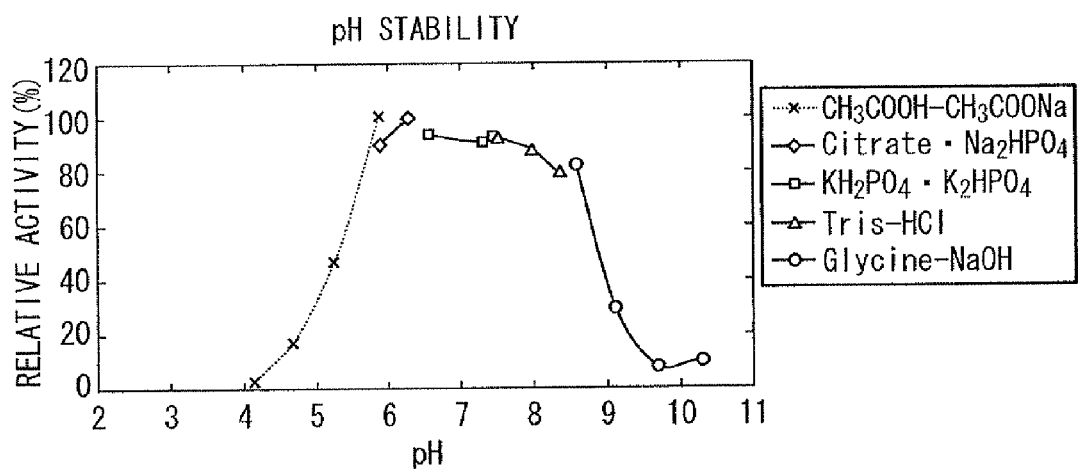
FIG. 4 a graph showing measurement results of pH stability of the sorbose dehydrogenase produced in Example 1.

(2) pH Stability:

The sorbose dehydrogenase was dissolved in each 50 mM buffer [i.e. an acetic acid-sodium acetate buffer (pH 4.14-5.91), a citric acid-sodium phosphate buffer (pH5.91-6.30), a potassium phosphate buffer (pH 6.59-7.47), a Tris-HCl buffer (pH 7.53-8.39), or a glycine-sodium hydroxide buffer (pH 8.61-10.30)]. The enzyme activity after the dissolved sorbose dehydrogenase was incubated at 40° C. for fifteen minutes was measured based on the above "method of measuring enzyme activity". The results are shown in FIG. 4. As shown in FIG. 4, the sorbose dehydrogenase was stable within a range of pH 5.9-8.6.

Figure 5:
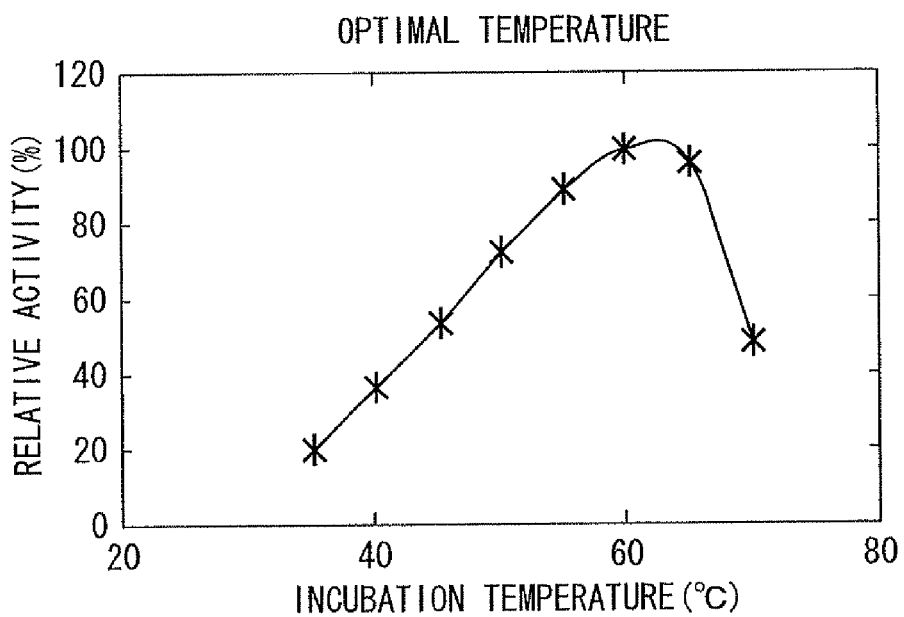
FIG. 5 is a graph showing measurement results of optimal temperature for the sorbose dehydrogenase produced in Example 1.

(3) Optimal Temperature:

The sorbose dehydrogenase was dissolved in a 50 mM potassium phosphate buffer, pH 7.0. The enzyme activity was measured while varying the temperature in the above "method of measuring enzyme activity" within a range of 35° C. to 70° C. The results are shown in FIG. 5. As shown in FIG. 5, the optimal temperature for the sorbose dehydrogenase was around 60° C.

(4) Temperature Stability

Figure 6:
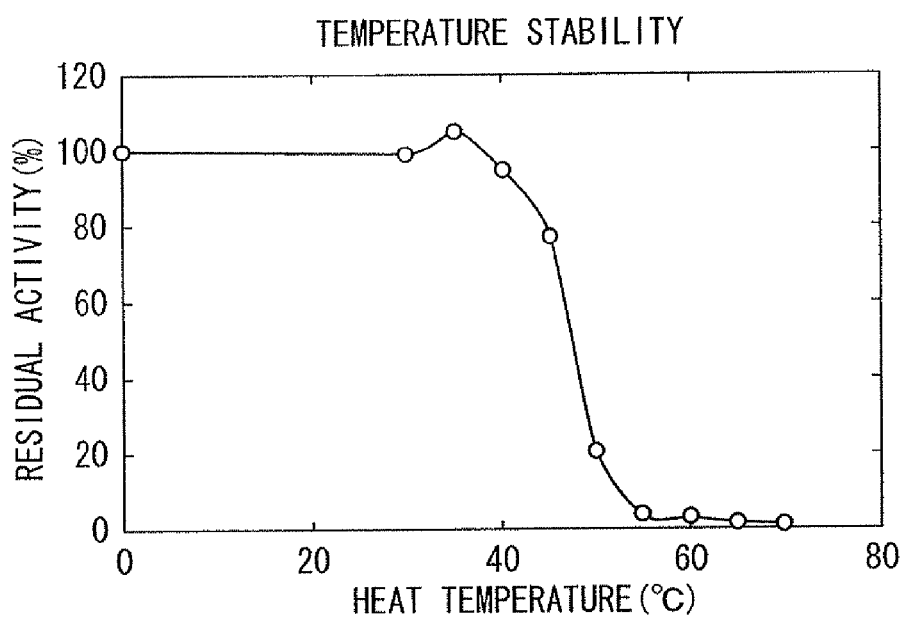
FIG. 6 is a graph showing measurement results of temperature stability of the sorbose dehydrogenase produced in Example 1.

The sorbose dehydrogenase was dissolved in a 50 mM potassium phosphate buffer, pH 7.0, containing 0.25% (w/v) "BL-9EX" (manufactured by Nikko Chemicals co., Ltd.) and 0.01 mM FAD. After the dissolved sorbose dehydrogenase was incubated at each point of temperature within 30° C. to 70° C. for ten minutes, the enzyme activity was measured based on the above "method of measuring enzyme activity" to obtain the residual ratio of enzyme activity. The results are shown in FIG. 6. As shown in FIG. 6, the sorbose dehydrogenase retained 77% of the enzyme activity even at 45° C., and was stable at about 45° C. or less.

(5) Substrate Specificity and Km Value:

When 1,5-AG, L-sorbose or other substrates shown in Table 4 (the final concentration was 167 mM for lactose, and 333 mM for any other substrate) was used as the substrate for the reaction solution for the activity measurement in the above "method of measuring enzyme activity", the activity thereof was measured by following the above "method of measuring enzyme activity" to obtain a relative reactivity. The results are shown as a relative value of each substrate with reference to the value of activity of L-sorbose as a standard.

TABLE 4

Substrate Specificity

| Substrate | Relative activity (%) |
|---|---|
| L-(−)-sorbose | 100 |
| 1,5-anhydroglucitol | 79.1 |
| Allyl alcohol | 3.80 |
| D-(−)-sorbose | 2.96 |
| 2-methyl-1-propanol | 2.06 |
| D-(+)-galactose | 1.69 |
| 1-butanol | 1.29 |
| D-(+)-glucose | 1.22 |
| Xylitol | 0.89 |
| 1-propanol | 0.75 |
| Lactose | 0.71 |
| 2-propanol | 0.39 |
| 2,3-butanediol | 0.26 |
| D-(+)-mannose | 0.15 |
| Ethanol | 0 |
| Glycerol | 0 |
| Maltose | 0 |
| D-(−)-fructose | 0 |

As shown in Table 4, the sorbose dehydrogenase had a strong effect on 1,5-AG and L-sorbose while the sorbose dehydrogenase had a weak effect on an allyl alcohol, D-sorbose, 2-methyl-1-propanol, D-galactose, 1-butanol, or D-glucose. Moreover, the sorbose dehydrogenase had little effect on xylitol, 1-propanol, lactose, 2-propanol, 2,3-butanediol, D-mannose, ethanol, glycerol, maltose, D-fructose, L-rhamnose, D-mannitol, D-sorbitol, D-ribose, D-xylose, L-arabinose, D-cellobiose, sucrose, D-trehalose, D-raffinose, inositol, meso-erythritol, 2-butanol, 2-pentanol, propylene glycol, or methanol.

Furthermore, the Km value of the sorbose dehydrogenase was 82.5 mM to 1,5-AG, and 65.6 mM to L-sorbose.

(6) Total Molecular Weight and Subunit Molecular Weight:

The total molecular weight of the sorbose dehydrogenase was analyzed with TSKgel BioAssist G4SWXL column (diameter 0.78 cm×length 30 cm; manufactured by Tosoh Corporation) at a flow rate of 0.5 mL/minute using a 50 mM potassium phosphate buffer, pH 7.5, containing 0.2 M NaCl in the mobile phase. By comparing the sorbose dehydrogenase with a molecular weight marker (manufactured by Oriental Yeast co., Ltd.) and another molecular weight marker (manufactured by Amersham Biosciences) and IgM (manufactured by Sigma), it was assumed that the sorbose dehydrogenase existed in a form having a total molecular weight of about 150 kDa or about 672 kDa.

By use of 10% polyacrylamide gel, the sorbose dehydrogenase was subjected to a SDS-polyacrylamide gel electrophoresis (SDS-PAGE) by following the method according to Laemmli et al. After the electrophoresis, the polyacrylamide gel was stained with Coomassie brilliant blue and the mobility of the sorbose dehydrogenase was compared with mobility of a molecular weight marker (manufactured by Amersham Biosciences). As a result, it was assumed that the subunit molecular weight of the sorbose dehydrogenase was about 59.6 kDa.

(7) Inhibitor:

Each additive shown in Table 5 was added to the reaction solution for the activity measurement in the above "method of measuring enzyme activity" in a final concentration of 1 mM, and the activity of the sorbose dehydrogenase was measured. The control was measured by following the aforementioned "method of measuring enzyme activity" without adding any additives. The activity value obtained when each of additives 1) to 39) was added thereto was calculated as a relative activity (%) where the activity value of the control was considered as 100%. The results are shown in Table 5.

TABLE 5

| Inhibitor | Final concentration (mM) | Relative activity (%) |
|---|---|---|
| Control: inhibitor not added. | 0 | 100 |
| 1) NaN$_3$ | 1.0 | 115 |
| 2) AlCl$_3$ | 1.0 | 109 |
| 3) 8-quinolinol | 0.3 | 106 |
| 4) EDTA-2Na | 1.0 | 102 |
| 5) Benzoic acid | 1.0 | 101 |
| 6) Fumaric acid | 1.0 | 99 |
| 7) LiCl | 1.0 | 98 |
| 8) H$_2$O$_2$ | 1.0 | 98 |
| 9) ZnCl$_2$ | 1.0 | 98 |
| 10) meso-tartaric acid | 1.0 | 94 |
| 11) KCN | 1.0 | 94 |
| 12) MgCl$_2$ | 1.0 | 93 |
| 13) CaCl$_2$ | 1.0 | 92 |
| 14) Urea | 1.0 | 92 |
| 15) CdCl$_2$ | 1.0 | 91 |
| 16) Aminoguanidine sulfate | 1.0 | 91 |
| 17) D-cycloserine | 1.0 | 90 |
| 18) FeCl$_3$ | 1.0 | 89 |
| 19) Tiron | 1.0 | 89 |
| 20) N-ethylmaleimide | 1.0 | 88 |
| 21) 2,2'-bipyridine | 1.0 | 88 |
| 22) SnCl$_2$ | 0.5 | 86 |
| 23) CoCl$_2$ | 1.0 | 86 |
| 24) Citric acid | 1.0 | 86 |
| 25) DL-tartaric acid | 1.0 | 86 |
| 26) NaCl | 1.0 | 85 |
| 27) DL-malic acid | 1.0 | 85 |
| 28) Iodoacetic acid | 1.0 | 83 |
| 29) PbCl$_2$ | 1.0 | 83 |
| 30) Maleic acid | 1.0 | 82 |
| 31) NiCl$_2$ | 1.0 | 80 |
| 32) BaCl$_2$ | 1.0 | 80 |
| 33) 1,10-phenanthroline | 1.0 | 77 |
| 34) 2-(p-)nitrobenzoic acid | 1.0 | 75 |
| 35) Acriflavin | 1.0 | 66 |
| 36) Triton X-100 | 1.0 | 39 |
| 37) MnCl$_2$ | 1.0 | 11 |
| 38) HgCl$_2$ | 1.0 | 0 |
| 39) CuCl$_2$ | 1.0 | 0 |

Based on results shown in Table 5, the sorbose dehydrogenase was remarkably inhibited by heavy metal ions ($Mn^{2+}$, $Hg^{2+}$ or $Cu^{2+}$). The relative activity was 66% when acriflavin was added.

(8) Identification of a Product of the Enzyme Reaction:

One and half mL of an enzyme reaction solution of a 50 mM potassium phosphate buffer, pH 7.5, containing 300 mM L-sorbose, 60 mM 1-methoxy-5-methylphenazinium methyl sulfate, 498 U/mL catalase (manufactured by Wako Pure Chemical Industries, Ltd.) and 3.87 U of sorbose dehydrogenase obtained in 2.6 was reacted for two hours at room temperature with stirring. The enzymes were removed with a centrifugal ultrafiltration device "Microcon YM-10" (manufactured by Amicon, molecular cutoff: 10,000), and the enzyme reaction solution was analyzed by high performance liquid chromatography. As a result, by comparison with an authentic sample for a retention time, it was identified that the product of the enzyme reaction was L-sorbosone. The L-sorbosone used as the authentic sample was chemically synthesized.

In addition, the analysis conditions of the high performance liquid chromatography were as follows.

Column: "High Performance Carbohydrate column" (manufactured by Waters Corporation).
Detection: RI.
Mobile phase: acetonitrile/distilled water=6:4 (containing 50 mM potassium phosphate buffer, pH 6.0).
Flow rate: 1.0 mL/min
Column temperature: 35° C.
Injection volume: 10 μL.
[Formulation of Standard Curve]

Figure 7:
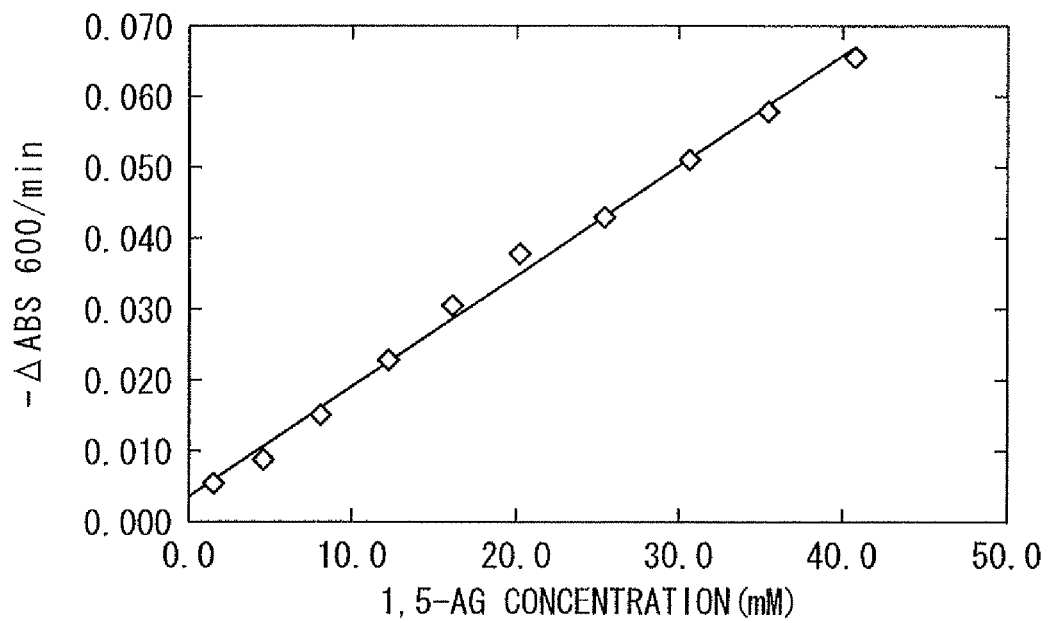
FIG. 7 is a graph showing a standard curve formulated in Example 1.

The substrate was substituted with 1,5-AG instead of L-sorbose in the aforementioned "method of measuring enzyme activity". While varying the final concentration of 1,5-AG within a range of 1.5-40.6 mM, changes in the absorbance were measured. By plotting the relationship between the concentration of 1,5-AG and changes in absorbance (Δ ABS600/min.), a standard curve was formulated as shown in FIG. 7. As shown in FIG. 7, it was revealed that 1,5-AG could be quantified with the sorbose dehydrogenase within a range of the final concentration of 1.5-40.6 mM.

[Coenzyme]

The sorbose dehydrogenase was subjected to acid treatment, and a flavin compound released from the protein of sorbose dehydrogenase by the acid treatment was analyzed by high performance liquid chromatography. The retention time of the flavin compound released from the sorbose dehydrogenase agreed with that of a standard of FAD. Consequently, it was found that the coenzyme for the sorbose dehydrogenase was FAD.

Example 2

Next, another example is described of production of the recombinant sorbose dehydrogenase using a substituted-type high-expression plasmid (hereinafter, referred to as pUCpTrcAGD1), and high-sensitive detection of 1,5-AG by way of activating the sorbose dehydrogenase.

Additionally, pUCpTrcAGD1 differs from pUCNNT2_AGD1 in that codons coding for glutamic acid (Glu) and phenylalanine (Phe) were inserted immediately after the start codon in the sorbose dehydrogenase gene, as described below.

Figure 8:
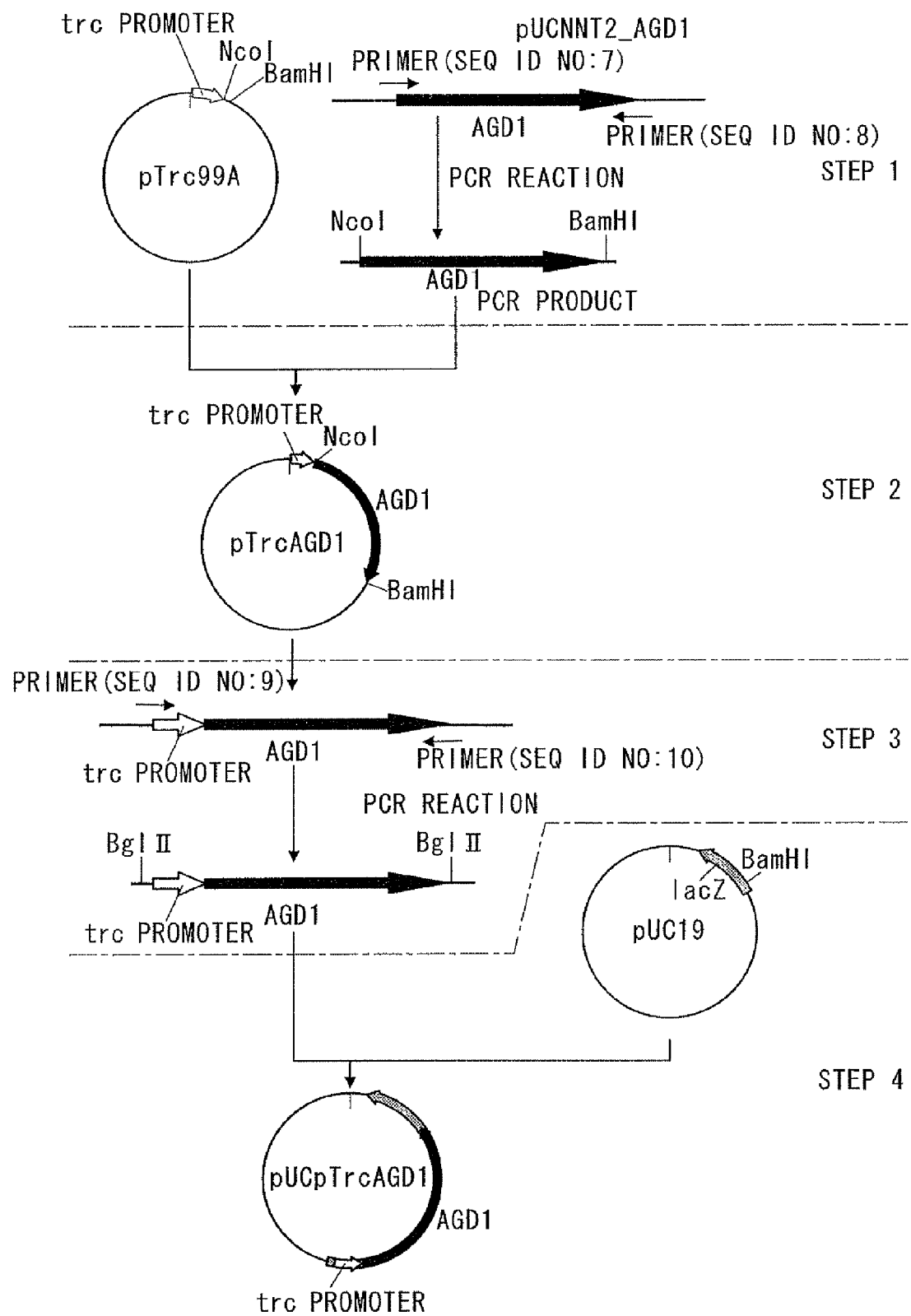
FIG. 8 is a schematic diagram that illustrates procedures for constructing a plasmid "pUCpTrcAGD1" used in production of a sorbose dehydrogenase in Example 2.

Hereinafter, a method of constructing plasmid pTrcAGD1 will be described in detail with reference to procedures briefly summarized in FIG. 8.

[1] Construction of Plasmid pTrcAGD1
1. PCR (Step 1 in FIG. 8)

PCR was conducted under the following conditions to obtain a PCR product including a substituted-type sorbose dehydrogenase gene of about 1.6 kbp.

Template: pUCNNT2_AGD1
Primers: DNAs represented by SEQ ID NO: 7 and SEQ ID NO: 8
Polymerase: Takara LA Taq (manufactured by Takara Bio Inc.)

In addition, the primer represented by SEQ ID NO: 7 included the restriction recognition site of NcoI and the inserted sequence of glutamic acid (gaa) and phenylalanine (ttc) while the primer represented by SEQ ID NO: 8 included the restriction recognition site of BamHI. The positional relationship of the primers is shown in Step 1 of FIG. 8.

Reaction Conditions:
a. Denaturation at 94° C. for two minutes (one cycle)
b. Denaturation at 94° C. for forty seconds
c. Annealing at 58° C. for thirty seconds
d. Extension at 72° C. for two minutes
e. Extension at 72° C. for five minutes (one cycle)
35 cycles of the reactions of b to d were conducted.

2. Purification of the PCR Product (Step 1 in FIG. 8).

The PCR product obtained in 1. was subjected to agarose gel electrophoresis to confirm the amplification of the product. The DNA of about 1.6 kbp, including the sorbose dehydrogenase gene was purified by using "QIAquick PCR Purification Kit" (manufactured by Qiagen).

3. Treatment with Restriction Enzymes (Step 1 in FIG. 8)

The DNA of about 1.6 kbp, including the sorbose dehydrogenase gene purified in 2. was treated with restriction enzymes NcoI and BamHI. The DNA of about 1.6 kbp, including the sorbose dehydrogenase gene, treated with the restriction enzymes was subjected to agarose gel electrophoresis to purify the DNA, and the DNA of about 1.6 kbp, including the sorbose dehydrogenase gene was extracted from the agarose gel by using "QIAquick Gel Extraction Kit" (manufactured by Qiagen).

A plasmid pTrc99A (manufactured by Amersham Biosciences) was treated with restriction enzymes NcoI and BamHI, and then, was purified by using "QIAquick PCR Purification Kit" (manufactured by Qiagen).

4. Ligation (Step 2 in FIG. 8)

The DNA of about 1.6 kbp, including the sorbose dehydrogenase gene and the pTrc99A treated with restriction enzymes in 3. was ligated by using "Ligation High" (manufactured by TOYOBO CO., LTD.) to construct a plasmid pTrcAGD1. The schematic diagram showing the plasmid pTrcAGD1 is shown in Step 2 of FIG. 8.

5. Transformation

E. coli JM109 competent cells (manufactured by Takara Bio Inc.) were transformed with the plasmid pTrcAGD1 constructed in 4. The transformed cells were inoculated on an LB plate, containing ampicillin sodium, and cultured at 37° C. overnight. The grown colonies were further cultured under the following conditions.

Culture medium: LB medium 10 mL
Culture container: a test tube (diameter 2.5 cm×length 20 cm)
Culture conditions: 30° C., twenty hours and 210 rpm Plasmids were extracted from the culture by using "QIAprep Spin Miniprep Kit" (manufactured by Qiagen). The plasmids were treated with restriction enzymes NcoI and BamHI, and the treated plasmids were subjected to agarose gel electrophoresis to confirm whether the sorbose dehydrogenase gene was inserted into the plasmids.

Additionally, the nucleotide sequence of the substituted-type sorbose dehydrogenase gene is shown as SEQ ID NO: 5 while the amino acid sequence thereof is shown as SEQ ID NO: 6.

[2] Construction of plasmid pUCpTrcAGD1
1. PCR (Step 3 in FIG. 8)

PCR was conducted under the following conditions to obtain a PCR product, including the trc promoter and the sorbose dehydrogenase gene (about 2.2 kbp in total).

Template: pTrcAGD1
Primers: DNAs represented by SEQ ID NO: 9 and SEQ ID NO: 10
Polymerase: Takara Ex Taq (manufactured by Takara Bio Inc.)

In addition, the primers of SEQ ID NO: 9 and SEQ ID NO: 10 included the BglII-recognition site as an adaptor sequence.

Reaction Conditions:
a. Denaturation at 96° C. for five minutes (one cycle)
b. Denaturation at 96° C. for forty seconds
c. Annealing at 58° C. for forty seconds
d. Extension at 72° C. for two minutes
e. Extension at 72° C. for five minutes (one cycle)
25 cycles of the reactions of b to d were conducted.

2. Purification of the Product from the Excised Gel (Step 3 in FIG. 8)

The PCR product obtained in 1. was subjected to agarose gel electrophoresis to purify the product. The DNA of about 2.2 kbp, including the trc promoter and the sorbose dehydrogenase gene was extracted from the agarose gel by using "QIAquick Gel Extraction Kit" (manufactured by Qiagen).

3. Treatment with Restriction Enzymes (Steps 3 and 4 in FIG. 8)

The DNA of about 2.2 kbp, including the trc promoter and the sorbose dehydrogenase gene purified from the agarose gel in 2. was treated with a restriction enzyme BglII. The DNA of about 2.2 kbp, including the trc promoter and the sorbose dehydrogenase treated with the restriction enzyme was subjected to agarose gel electrophoresis to purify the DNA, and the DNA of about 2.2 kbp, including the trc promoter and the sorbose dehydrogenase gene was extracted from the agarose gel by using "QIAquick Gel Extraction Kit" (manufactured by Qiagen).

A plasmid pUC19 was treated with a restriction enzyme BamHI, and then, subjected to dephosphorylation treatment.

4. Ligation (Step 4 in FIG. 8)

The DNA of about 2.2 kbp, including the trc promoter and the sorbose dehydrogenase gene, and the pUC 19 treated with restriction enzymes in 3. were ligated with "Ligation High" (TOYOBO CO., LTD.) to construct a pUCpTrcAGD1. A schematic diagram showing the plasmid pUCpTrcAGD1 is shown in Step 4 of FIG. 8.

5. Transformation

E coli JM109 competent cells (manufactured by Takara Bio Inc.) were transformed with the plasmid pUCpTrcAGD1 constructed in 4. The transformed competent cells were inoculated on an LB plate, containing ampicillin sodium, and cultured at 37° C. overnight. Grown colonies were cultured under the following conditions.

Culture medium: LB medium 10 mL
Culture container: a test tube (2.5 cm in diameter×20 cm in length)
Culture conditions: 30° C., twenty hours and 200 rpm Plasmids were extracted from the culture by using "QIAprep Spin Miniprep Kit" (manufactured by Qiagen). The plasmids were treated with restriction enzymes EcoRI and PstI, and the treated plasmids were subjected to agarose gel electrophoresis to confirm whether the trc promoter and the sorbose dehydrogenase gene were inserted into the plasmids.

One (hereinafter, referred to as "E. coli JM109/pUCpTrcAGD1") of the E. coli clones (it was confirmed that the trc promoter and the sorbose dehydrogenase gene were introduced into the clones) was used in "Production of substituted-type sorbose dehydrogenase", as described below.

With respect to the plasmid extracted from the E. coli JM109/pUCpTrcAGD1, the nucleotide sequence of the sorbose dehydrogenase gene-coding region was determined. The determined nucleotide sequence is shown as SEQ ID NO: 5 while the amino acid sequence thereof is shown as SEQ ID NO: 6.

Based on confirmation of the nucleotide sequence, it was confirmed that gaa (glutamic acid) and ttc (phenylalanine) were inserted immediately after the start codon of the inserted sorbose dehydrogenase in its reading frame in that order.

Furthermore, it was confirmed that the $51^{st}$ nucleotide of cytosine (C), the $108^{th}$ nucleotide of guanine (G), and the $168^{th}$ nucleotide of guanine (G) in the sorbose dehydrogenase-coding region of the pUCNNT2_AGD1 were substituted with thymine (T), adenine (A) and adenine (A), respectively, in pUCpTrcAGD1. However, there were no mutations such as substitution owing to the nucleotide substitutions in the amino acid sequence of the coded sorbose dehydrogenase except that the two amino acids were inserted therein.

[3] Production of Substituted-Type Sorbose Dehydrogenase

1. Culture

Bacterial cell: genetically-modified E. coli JM109/pUCp-TrcAGD1

1.1 Seed Culture

One hundred mL of an LB medium was charged to a 500 mL Erlenmeyer flask, and this was autoclaved. An ampicillin sodium solution sterilized by filtration was added thereto immediately before use in a final concentration of 0.01% (w/v). The genetically-modified E. coli JM109/pUCpTrcAGD1 was inoculated into the LB medium with a platinum loop, and cultured at 25° C. with shaking (120 rpm). The culture medium twenty-one hours after culturing was started was used as an inoculum for main culture.

1.2 Main Culture

One hundred mL of an LB medium was charged to a 500 mL Erlenmeyer flask, and this was autoclaved. An ampicillin sodium solution sterilized by filtration was added thereto immediately before use in a final concentration of 0.01% (w/v). In this way, forty flasks containing the LB medium were prepared. 2 mL of the seed culture prepared in 1.1 was inoculated into each flask. After these were cultured at 25° C. with shaking (120 rpm) for three hours, a filter-sterilized isopropyl β-D-1-thiogalactopyranoside solution was added to culture medium in each flask in a final concentration of 0.0024% (w/v), and these were further cultured at 25° C. with shaking for twenty-one hours. After culturing, the bacterial cells were harvested by using a centrifuge.

2. Purification

The substituted-type sorbose dehydrogenase was extracted and purified from the bacterial cells obtained by the above culture through the following purification steps. The results are shown in Table 6.

The activity of the sorbose dehydrogenase was measured based on the "method of measuring enzyme activity" described in Example 1.

TABLE 6

| Purification step | Total activity (U) | Specific activity (U/mg) | Yield (%) | Fold |
|---|---|---|---|---|
| CFE | 883 | 0.19 | 100 | 1.00 |
| Ammonium sulfate precipitation | 517 | 0.24 | 58.6 | 1.26 |
| Weak anion-exchange chromatography (DEAE FF) | 502 | 0.91 | 56.9 | 4.79 |
| Desalting and Concentration | 322 | 0.94 | 36.5 | 4.95 |

2.1 Preparation of Cell-Free Extract (CFE)

Three hundred and sixty mL of a 50 mM potassium phosphate buffer, pH 7.5 was added to bacterial cells obtained in the main culture of 1.2 to prepare cell suspension.

The cell suspension was divided equally into four portions. With respect to the divided portions, the bacterial cells were disrupted with a sonication disruption apparatus ("IN-SONATOR 201M" manufactured by Kubota Corporation) at the output power of 180 W for thirty minutes. Each of the treated solutions was combined, and the combined solution was centrifuged at 11,000×g at 4° C. for thirty minutes to recover 355 mL of CFE.

2.2 Ammonium Sulfate Fractionation

BL-9EX was added to the CFE recovered in 2.1 in a final concentration of 0.25% (v/v), and this was dissolved while being stirred for thirty minutes. 51.12 g of ammonium sulfate was stepwise added to the CFE in an ice bath, thereby dissolving it, until the saturated concentration reached 25%. The CFE was further stirred for thirty minutes after ammonium sulfate was dissolved. The dissolved solution was centrifuged at 11,000×g at 4° C. for thirty minutes, and 370 mL of the supernatant was recovered. Then, 34.41 g of ammonium sulfate was stepwise added to the supernatant in an ice bath, thereby dissolving it, until the saturated concentration reached 40%. The supernatant was further stirred for thirty minutes after ammonium sulfate was dissolved, and the supernatant was allowed to stand at 4° C. overnight.

2.3 Dialysis

The ammonium sulfate precipitate was recovered by centrifugation (11,000×g, 4° C., thirty minutes). The recovered ammonium sulfate precipitate was dissolved in 10 mL of a 50 mM sodium phosphate buffer, pH 7.5. The dissolved precipitate was put into a dialysis tube, and this was dialyzed with a dialysis buffer (20 mM Tris-HCl, pH 7.5, containing 20% glycerol).

2.4 Centrifugation

An insoluble was present inside the dialysis tube. Therefore, the insoluble was removed by centrifugation (27,000×g, 4° C., and fifteen minutes), and 21 mL of the supernatant was recovered.

2.5 Weak Anion-Exchange Chromatography (DEAE Sepharose Fast Flow)

The supernatant recovered in 2.4 was charged to 320 mL (column size: f 2.6 cm×60 cm in length) of a weak anion-exchange resin "DEAE Sepharose Fast Flow" (manufactured by GE Healthcare Bio-Sciences K.K.) equilibrated with an equilibration buffer (20 mM Tris-HCl, pH 7.5, containing 20% glycerol). After charging, the resin was washed with three resin-bed volume of buffer (20 mM Tris-HCl, pH 7.5, containing 20% glycerol) for washing. Then, the objective protein was gradient-eluted with two types of elution buffers (buffer 1: 20 mM Tris-HCl, pH 7.5, containing 20% glycerol; and buffer 2: 20 mM Tris-HCl, pH 7.5, containing 20% glycerol and 1 M NaCl) (their volume was 5 times the bed volume of resin), thereby recovering 262 mL of active fractions.

2.6 Desalting and Concentration

The active fractions obtained in 2.5 were concentrated into 21.5 mL by using a ultrafiltration equipment "model 8200" (manufactured by Amicon, molecular cutoff: 100,000). The concentrated solution was put into a dialysis tube, and dialyzed with a dialysis buffer (50 mM HEPES, pH 7.5) to substitute the buffer. The solution was further concentrated into 2.7 mL by centrifugation (2,700×g, 4° C., three hours) with an ultrafiltration equipment "Vivaspin 20" (manufactured by Vivascience, molecular cutoff: 100,000). In this way, 322 U of the substituted-type sorbose dehydrogenase was obtained.

[4] Activation of Substituted-Type Sorbose Dehydrogenase

The sorbose dehydrogenase (hereinafter, referred to as substituted-type enzyme) produced in [3] ("Production of substituted-type sorbose dehydrogenase") was treated with 1-methoxy-5-methylphenazinium methyl sulfate (1m-PMS) in the manner described below to activate the substitute-type enzyme.

A 50 mM HEPES buffer, pH 7.5 (1.765 mL) and 0.12 mL of 1m-PMS aqueous solution (20 mM) were added to 0.115 mL of the substituted-type enzyme solution (conc. 119 U/mL) produced in [3], and these were mixed. Then, the mixed solution was incubated in a refrigerator overnight to activate the enzyme. After activation, the total portion of the activated enzyme solution was applied to a centrifugal concentrator "Vivaspin 20" (manufactured by Vivascience, molecular cutoff: 50,000), and the solution was diluted with 10 mL of a 50 mM HEPES buffer, pH 7.5, therein. Then, the spin column was loaded into a centrifuge, and centrifuged at 4,500 rpm for forty-five minutes to concentrate the solution to the total volume of about 0.3 mL. The concentrated solution was diluted by addition of 10 mL of a 50 mM HEPES buffer, pH 7.5, and then, the solution was centrifuged again to concentrate the solution, thereby removing 1m-PMS. In addition, the same procedure was repeated two times to completely remove 1m-PMS. Finally, a 50 mM HEPES buffer, pH 7.5 was added to adjust the total volume of the solution to 4 mL, and the concentration of the activated substituted-type enzyme was adjusted to 3.4 U/mL.

[5] Confirmation of Activation Effect

R2 reagents described in Example 3 ("clinical method of determining 1,5-AG") were prepared by using the enzyme activated with 1m-PMS and untreated enzyme, respectively. By using R2 reagents, 1,5-AG standard solutions of 0 µg/mL and 50 µg/mL were measured, and the strength of the color development was compared between samples. The increase in absorbance for the 1,5-AG standard solution of 50 µg/mL was 0.064 in the non-activated enzyme while the increase was 0.248 (about four folds) in the activated enzyme. It was revealed that the enzyme was activated about four times.

Example 3

[1] Clinical Method of Determining 1,5-AG

Considering the application to an automatic biochemistry analyzer used widely in clinical laboratory tests, a determination method on the minimum scale was constructed.

In advance, determination reagents having the following compositions, i.e. R1-1 reagent (glucose-eliminating agent), R1-2 reagent (1m-PMS aqueous solution) and R2 reagent (1,5-AG detection reagent) were prepared.

Nine µL of a 1,5-AG standard solution or a clinical sample (i.e. test sample) and 200 µL of R1-1 reagent were added to a test tube, and these were stirred. The mixture was reacted in a water bath at 37° C. for five minutes. After the reaction, 10 µL of R1-2 reagent and 100 µL of R2 reagent were added thereto. The mixture was stirred, and the reaction solution was immediately transferred to a cell for a spectrophotometer. The cell was set in a cell holder heated to 37° C., and changes in the absorbance at 450 nm were measured for five minutes.

The clinical samples used in the present example were serums collected from a healthy person and a diabetic.

Reagent Composition

R1-1 Reagent (Glucose-Eliminating Agent)

| | |
|---|---|
| Potassium chloride | 49.6 mM |
| Sodium chloride | 100 mM |
| EDTA•2Na | 0.1 mM |
| Phosphoenolpyruvic acid | 8.01 mM |
| ATP | 0.99 mM |
| Magnesium chloride | 7.38 mM |
| Pyruvate kinase (TOYOBO CO., LTD.) | 5 U/mL |
| Glucokinase (UNITIKA, LTD.) | 4 U/mL |
| WST-1 | 0.95 mM |
| HEPES buffer | 50 mM (pH 7.5) |

R1-2 Reagent (1m-PMS Aqueous Solution)

| 1m-PMS | 0.4 mM |
|---|---|

R2 Reagent (1,5-AG Detection Agent)

| Substituted-type enzyme | 3.4 U/mL |
|---|---|
| HEPES buffer | 50 mM (pH 7.5) |

[2] Formulation of Standard Curve

Figure 9:
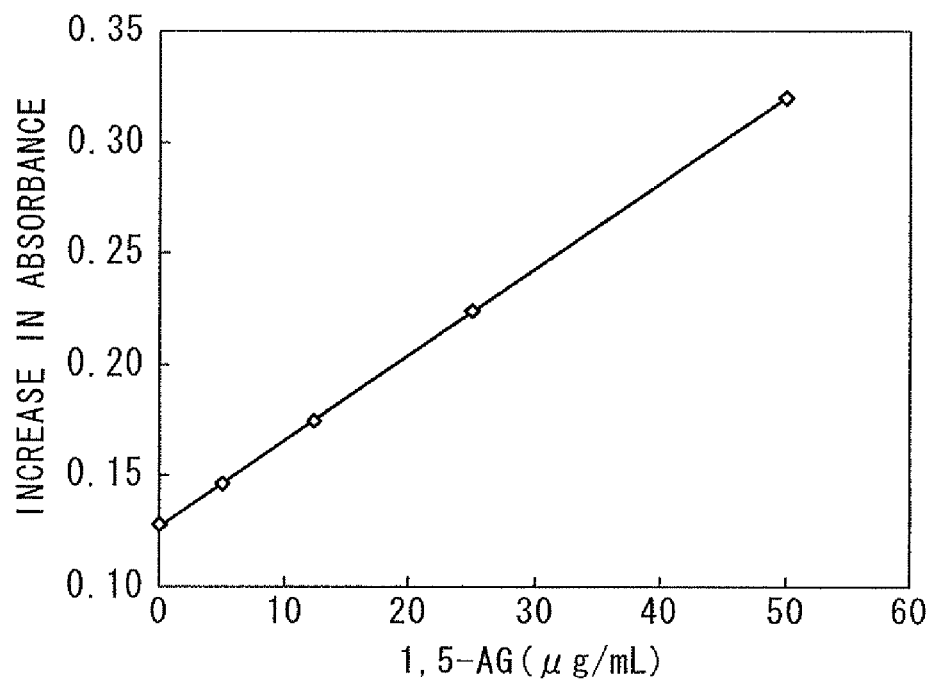
FIG. 9 is a graph showing a standard curve formulated in Example 2.

By using a serum-based matrix, 1,5-AG standard solutions of 0, 5, 12.5, 25 and 50 µg/mL were prepared. The 1,5-AG standard solutions were measured by the above-described clinical method of determining 1,5-AG, and a standard curve was formulated as shown in FIG. 9. The increment in absorbance is shown in Table 7 with respect to each standard solution.

TABLE 7

| | 1,5-AG (µg/mL) | | | | |
|---|---|---|---|---|---|
| | 0 | 5 | 12.5 | 25 | 50 |
| Increment in absorbance | 0.128 | 0.146 | 0.175 | 0.224 | 0.320 |

[3] Measurement in Clinical Sample

Twenty serum samples collected from healthy volunteer and diabetic patients were subjected to the measurement according to the above-described clinical method of determining 1,5-AG (present method), and the clinical method was compared with results obtained by measuring the samples with a previously-established 1,5-AG measurement kit "Lana 1,5AG Auto Liquid". The results are shown in Table 8 and FIG. 10.

TABLE 8

| Sample No. | AUTO LIQUID (µg/mL) | Present method (µg/mL) |
|---|---|---|
| No. 73 | 1.1 | 3.1 |
| No. 1 | 4.5 | 6.5 |
| No. 5 | 6.5 | 9.1 |
| No. 9 | 7.8 | 14.3 |
| S-5 | 9.7 | 13.5 |
| No. 42 | 10.4 | 11.2 |
| S-4 | 12.4 | 16.1 |
| No. 11 | 14.7 | 16.1 |
| S-1 | 15.1 | 18.5 |
| S-3 | 16.5 | 20.8 |
| No. 14 | 17.1 | 23.7 |
| No. 15 | 20.8 | 19.5 |
| No. 23 | 21.7 | 30.7 |
| No. 25 | 23.6 | 26.6 |
| S-2 | 26.4 | 35.7 |
| S-6 | 29.4 | 36.2 |
| No. 29 | 30.1 | 34.1 |
| S-7 | 31.8 | 30.7 |
| S-8 | 33.6 | 35.2 |
| No. 33 | 36.2 | 38.5 |

Figure 10:
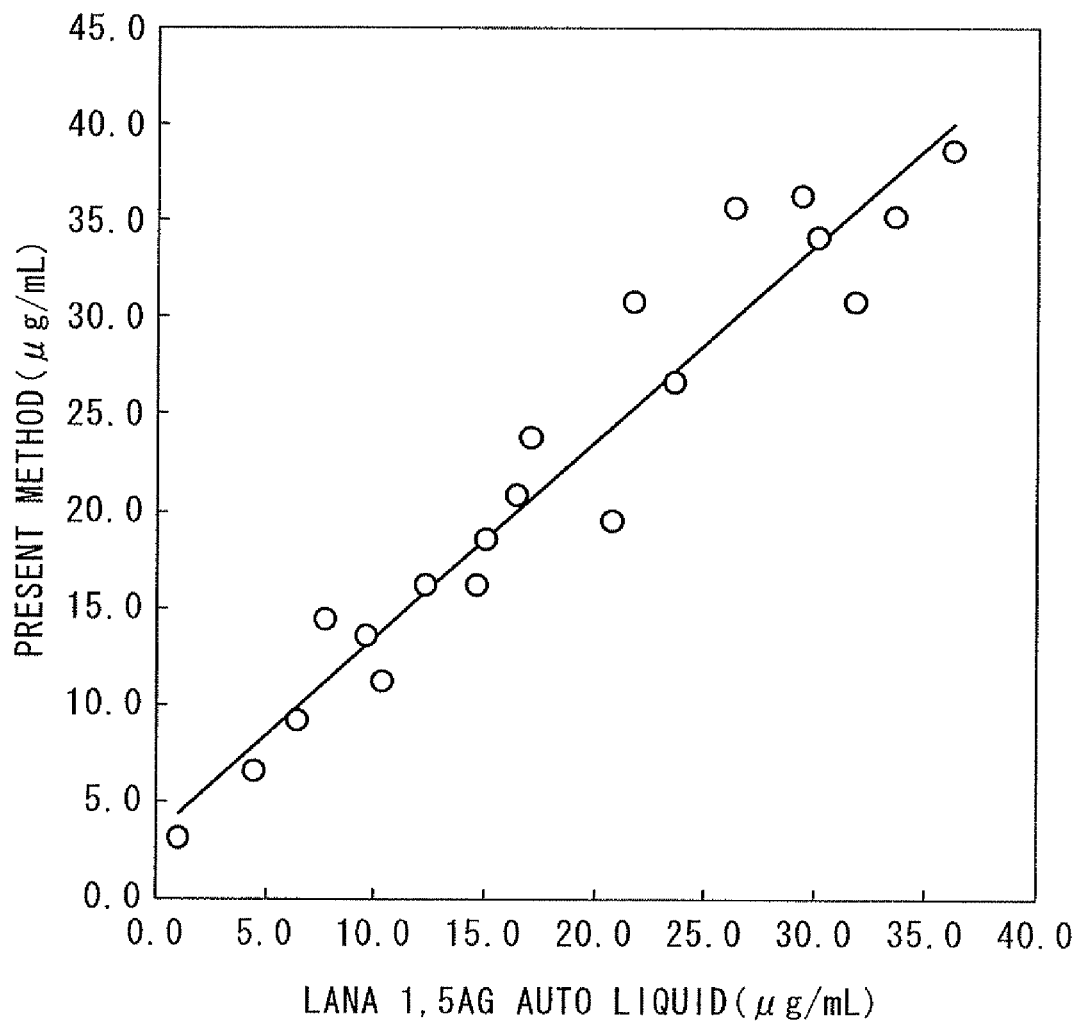
FIG. 10 is a graph showing results measured in Example 3 using the sorbose dehydrogenase produced in Example 2 with respect to clinical samples.

As shown in the graph of FIG. 10, a good correlation was found between the measurement values of both methods where the correlation formula was y (present method)= 1.0124×(Lana 1,5AG Auto Liquid)+3.3199, and the correlation coefficient (r) was 0.964.

INDUSTRIAL APPLICABILITY

According to the method of determining 1,5-AG and the reagent composition for determining 1,5-AG of the present invention, 1,5-AG, which is a control marker for diabetes, can be quantified with high accuracy. By applying the present invention to clinical samples such as blood plasma, serum, cerebrospinal fluid or urine, diagnosis of diabetes can be quickly and simply achieved.

Therefore, the present invention has high industrial applicability.

The invention claimed is:

1. A method of determining a quantity of 1,5-anhydroglucitol in a sample, comprising using
   (a) a recombinant protein which consists of amino acid sequence SEQ ID NO: 2; or
   (b) a recombinant protein which consists of amino acid sequence having a homology of at least 85% with the amino acid sequence SEQ ID NO: 2 and which has sorbose dehydrogenase activity.

2. The method of determining 1,5-anhydroglucitol according to claim 1, wherein the recombinant protein is originated from a bacterium that belongs to the genus *Sinorhizobium*.

3. The method of determining 1,5-anhydroglucitol according to claim 1, wherein the recombinant protein is originated from *Sinorhizobium* sp. 97507 PERM BP-10843.

4. The method of determining 1,5-anhydroglucitol according to claim 1, wherein, assuming that the reactivity of the recombinant protein to sorbose is 100%, the reactivity of the recombinant protein to 1,5-anhydroglucitol is 10% or higher.

5. The method of determining 1,5-anhydroglucitol according to claim 4, wherein, assuming that the reactivity of the recombinant protein to 1,5-anhydroglucitol is 100%, the reactivity of the recombinant protein to D-glucose is 10% or less.

6. The method of determining 1,5-anhydroglucitol according to claim 1, wherein 1,5-anhydroglucitol included in a sample is affected by the recombinant protein in the presence of a chromogenic substrate, and the amount of the reacted chromogenic substrate is measured.

7. The method of determining 1,5-anhydroglucitol according to claim 6, wherein D-glucose in the sample is removed before 1,5-anhydroglucitol included in the sample is affected by the recombinant protein.

8. The method of determining 1,5-anhydroglucitol according to claim 7, wherein 1,5-anhydroglucitol included in the sample is affected in the presence of the chromogenic substrate and an electron carrier.

9. The method of determining 1,5-anhydroglucitol according to claim 8, wherein 1 to 500 units of the recombinant protein is added to 1 mL of the sample where the enzyme activity of the recombinant protein measured using 1,5-anhydroglucitol as a substrate is defined as the base unit.

10. The method of determining 1,5-anhydroglucitol according to claim 8, wherein the recombinant protein is activated with the electron carrier before 1,5-anhydroglucitol included in the sample is affected by the recombinant protein.

* * * * *